(12) United States Patent
Rubinson et al.

(10) Patent No.: US 9,682,225 B2
(45) Date of Patent: Jun. 20, 2017

(54) POLYMER FILM BIOELECTRODES AND METHODS OF MAKING AND USING THE SAME

(75) Inventors: Judith F. Rubinson, Bethesda, MD (US); Yohani P. Kayinamura, Arlington, VA (US); Anthony D. Kammerich, Battlefield, MO (US); Yasmin N. Srivastava, Sugar Land, TX (US)

(73) Assignee: Georgetown University, Washington, DC (US)

( * ) Notice: Subject to any disclaimer, the term of this patent is extended or adjusted under 35 U.S.C. 154(b) by 1007 days.

(21) Appl. No.: 13/578,741

(22) PCT Filed: Feb. 11, 2011

(86) PCT No.: PCT/US2011/000246
§ 371 (c)(1),
(2), (4) Date: Sep. 19, 2012

(87) PCT Pub. No.: WO2011/100059
PCT Pub. Date: Aug. 18, 2011

(65) Prior Publication Data
US 2013/0001090 A1 Jan. 3, 2013

Related U.S. Application Data

(60) Provisional application No. 61/303,763, filed on Feb. 12, 2010, provisional application No. 61/358,178, filed on Jun. 24, 2010.

(51) Int. Cl.
*A61B 5/04* (2006.01)
*A61N 1/04* (2006.01)

(52) U.S. Cl.
CPC .................................. *A61N 1/04* (2013.01)

(58) Field of Classification Search
CPC .. A61N 1/0551; A61N 1/0529; A61N 1/0534; A61N 1/0531; A61N 1/0539; A61B 5/04001; A61B 2018/00434
(Continued)

(56) References Cited

U.S. PATENT DOCUMENTS 4,774,029 A * 9/1988 Poulin ..................... C07C 57/04
252/500
6,552,101 B1 * 4/2003 Roitman et al. ............... 522/167
(Continued)

OTHER PUBLICATIONS

International Search Report (PCT/ISA/210) issued on Jun. 9, 2011, for International Application No. PCT/US11/00246.
(Continued)

*Primary Examiner* — Brian M Antiskay
(74) *Attorney, Agent, or Firm* — RatnerPrestia

(57) ABSTRACT

Bioelectrodes, methods of making bioelectrodes and methods of using bioelectrodes are provided. The bioelectrodes have an electrically-conductive substrate coated with an electroconductive polymer. The bioelectrode exhibits ohmic behavior over a range of about 1 Hz to about 100 KHz, where ohmic behavior means that the value of the impedance is independent of the signal frequency over the range of interest. The bioelectrode can transmit or receive an electrical signal between the electrically conductive substrate and the biological component through the conductive polymer.

12 Claims, 23 Drawing Sheets

Comparision of PEDOT behavior after electropolymerization onto the different substrates. Electropolymerization Potential: 1300 mV vs. Ag/AgCl; EDOT: 0.0125 M in acetonitrile; Dopant: 0.1M BF$_4^-$ in acetonitrile; Electropolymerization time: 90 sec.

Solution conditions for EIS measurements: same as used in Figure 9

(58) Field of Classification Search
USPC ........ 600/372–373, 377–378, 393, 544–545; 607/115–118
See application file for complete search history.

(56) References Cited

U.S. PATENT DOCUMENTS

| | | |
|---|---|---|
| 2003/0143461 A1 | 7/2003 | Poehler et al. |
| 2005/0048651 A1 | 3/2005 | Ryttsen et al. |
| 2007/0060815 A1 | 3/2007 | Martin et al. |
| 2007/0185548 A1 | 8/2007 | Zdeblick |
| 2009/0292325 A1* | 11/2009 | Cederna ................ A61N 1/05 607/2 |
| 2010/0125315 A1 | 5/2010 | Parramon et al. |

OTHER PUBLICATIONS

European Search Report dated Aug. 28, 2013 in corresponding European Application No. EP11742577.

Ovadia M., et al., "Investigation of a semiconductor bioelectrode with Ohmic behavior in vivo: Impedance spectroscopy of p-type semiconductor electrodes in perfused living heart" Chemical Physics Letters, Elsevier BV, NL, vol. 419, No. 1-3 (2006) pp. 277-287, XP025013063.

European Communication Pursuant to Article 94(3) EPC mailed Jul. 7, 2015 for European Application No. 11 742 577.7.

* cited by examiner

Figure 1: Schematic of an exemplary embodiment of a polymer film electrode
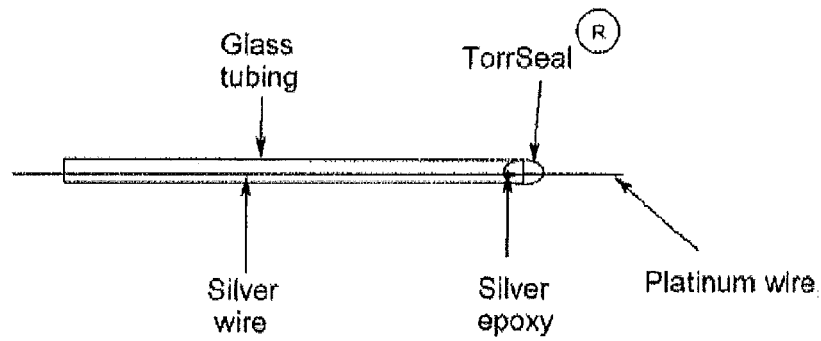
a) electrode without the electrically-conductive polymer.
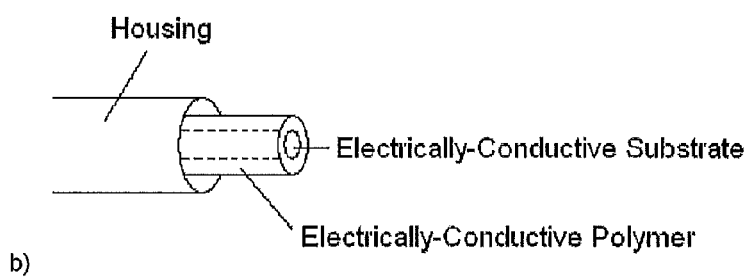
b)
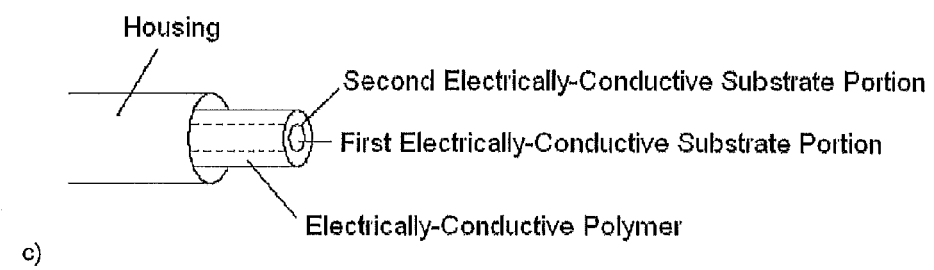
c)

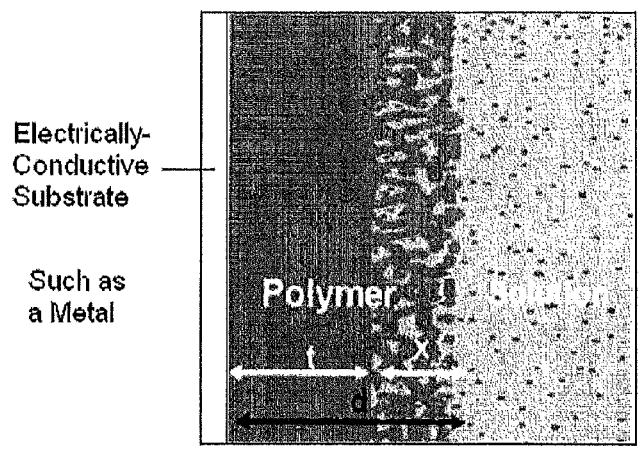
Figure 2: Morphological model of PEDOT film. t = compact layer, x = porous layer and d = film thickness
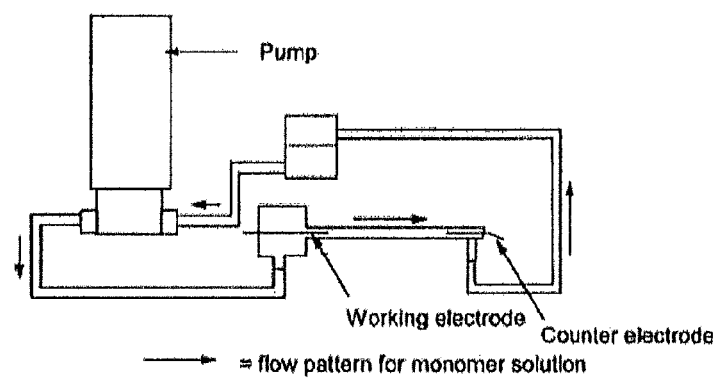
Figure 3: Schematic of flow-cell setup for producing electrode having a fiber

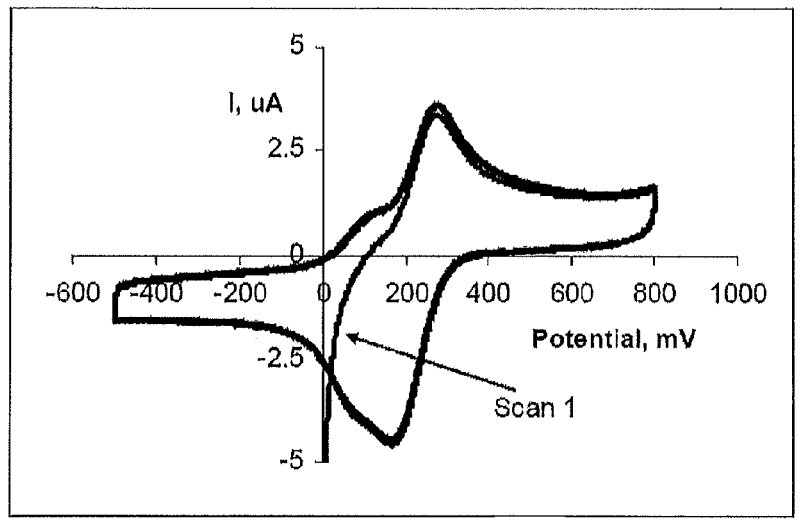
Figure 4: Cyclic voltammogram of $Fe(CN)_6^{4-}/Fe(CN)_6^{3-}$ at PEDOT/BF$_4$ electrode (Supporting electrolyte: 0.1 M KCl)
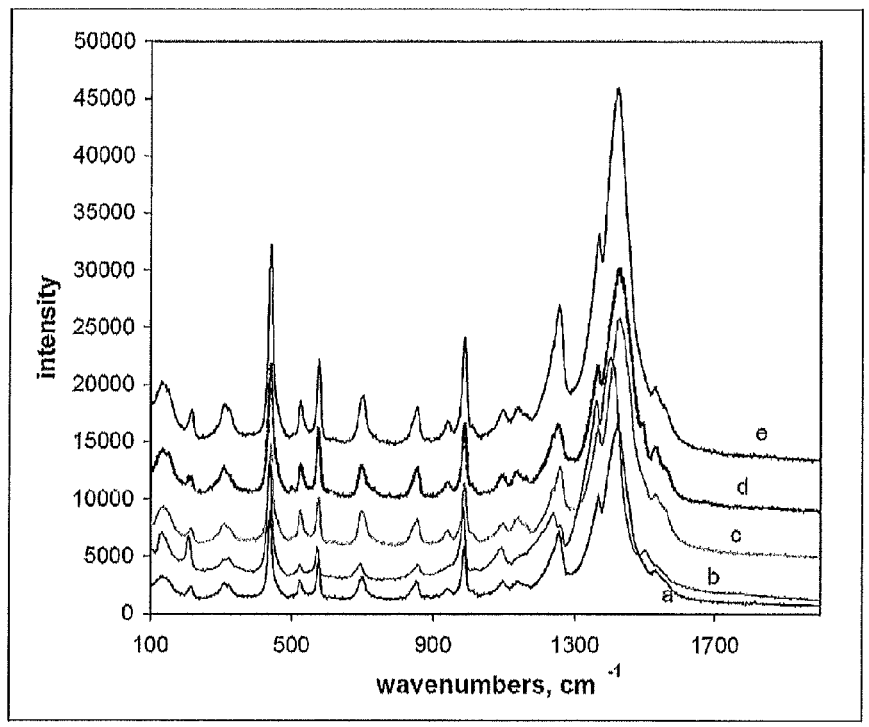
Figure 5: Raman spectra of PEDOT doped with various counterions:
(a) poly(styrene sulfonate); (b) p-toluene sulfonate; (c) hexafluorophosphate; (d) perchlorate; (e) tetrafluoroborate

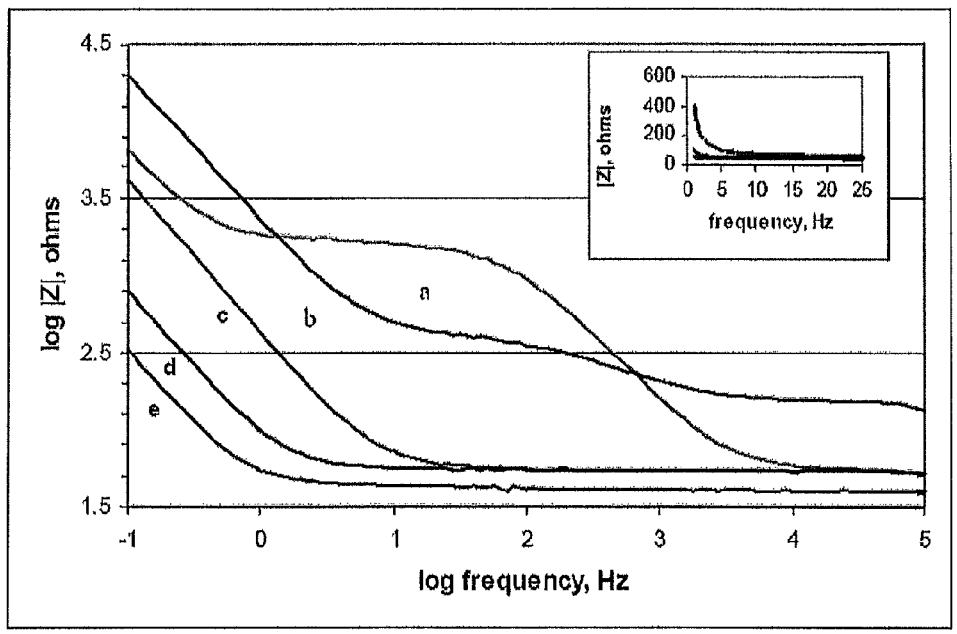

Figure 6: Bode plot from electrodes prepared with different counterions:
(a) poly(styrene sulfonate); (b) p-toluene sulfonate; (c) hexafluorophosphate; (d) perchlorate; (e) tetrafluoroborate.
The inset shows the behavior at low (<25 Hz) frequencies

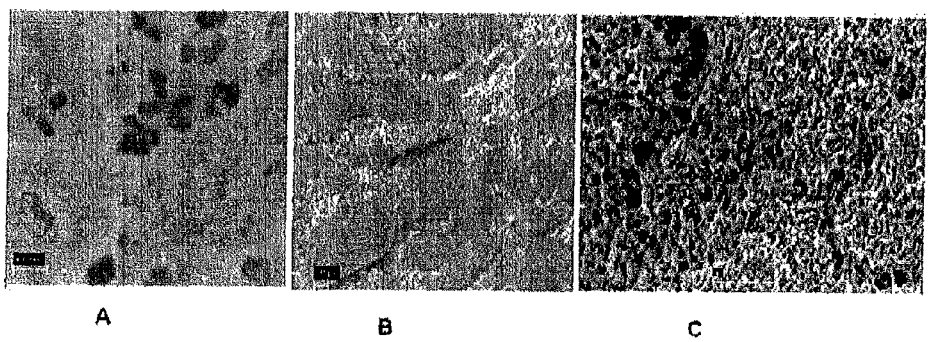

Figure 7: SEM of of the substrate/electrically-conductive polymer interface (a) and the surface of the electrically-conductive polymer (b and c) at different deposition times axis of wire

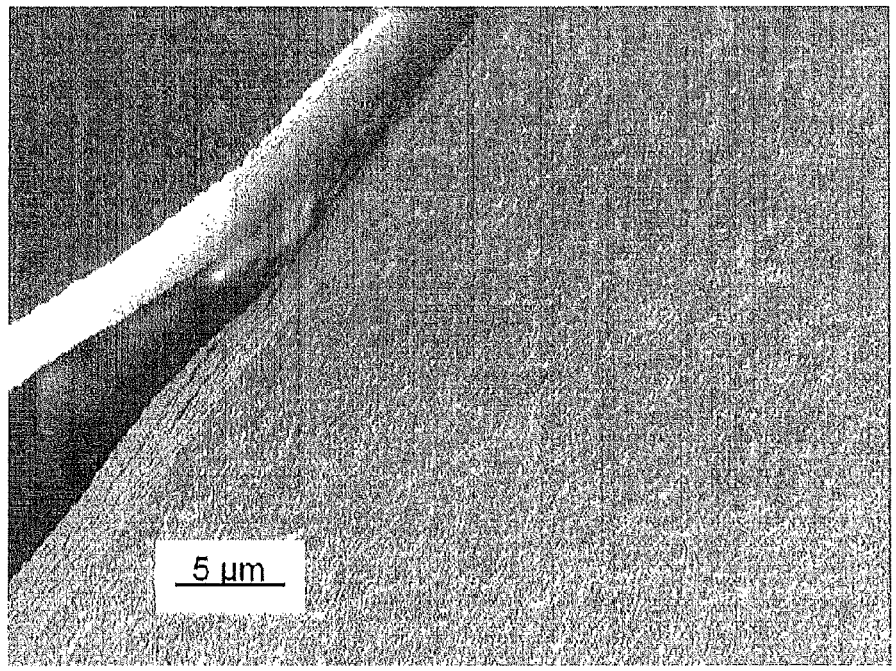
Figure 8g
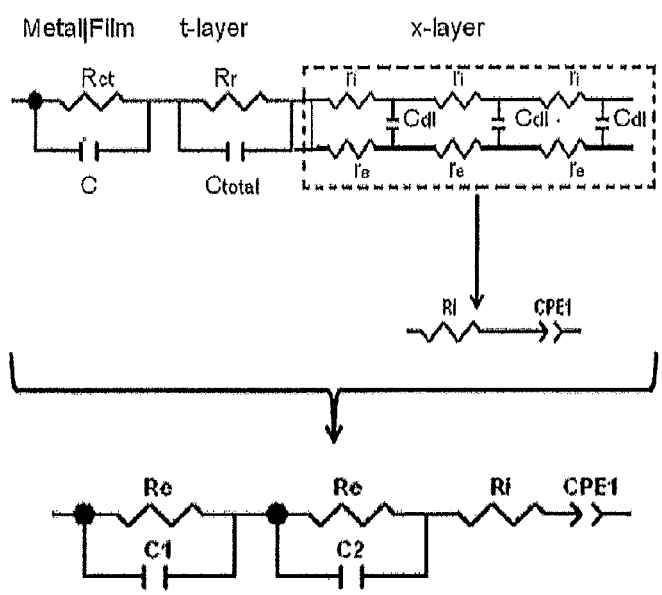
Figure 9. Proposed equivalent circuit for a two layer morphology (PEDOT/$BF_4^-$ electrodes produced using exemplary conditions as defined herein

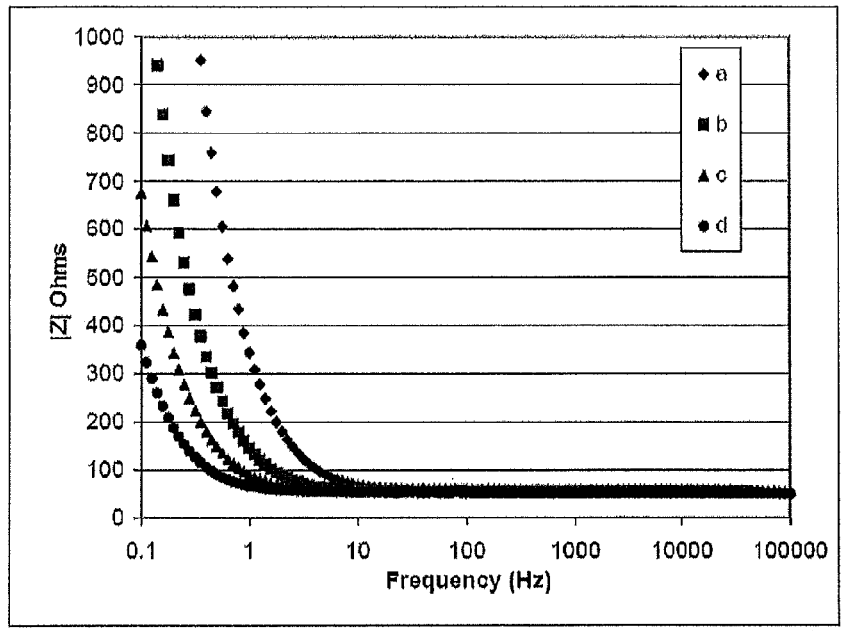

Figure 10: Bode plots for electrodes prepared with varying electropolymerization times. a) 30 seconds, b) 60 seconds, c) 90 seconds, d) 120 seconds. The EDOT monomer and counterion concentrations were 0.0125 M and 0.1 M, respectively, during polymerization

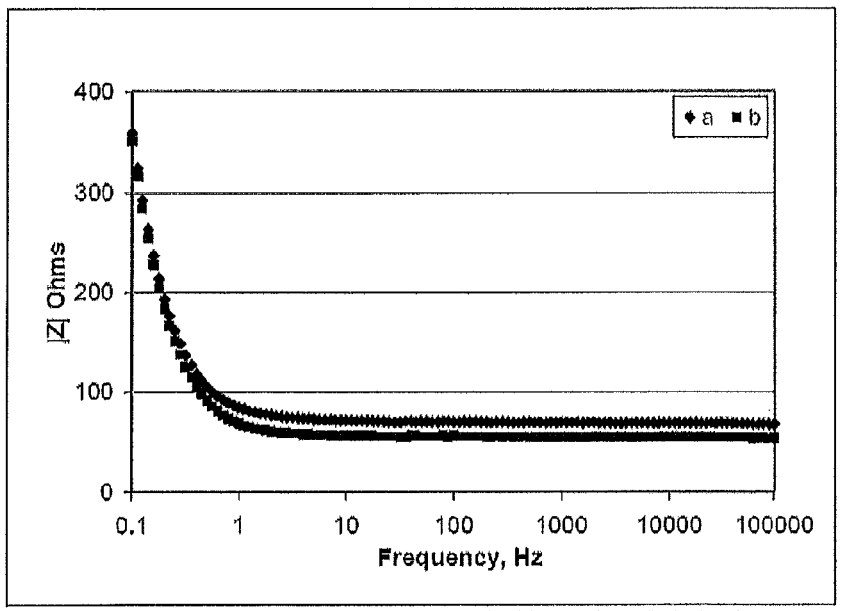

Figure 11: Bode plots for electrodes prepared with varying TBABF$_4$ dopant concentrations. a) 0.1 M; b) 0.05 M. The monomer concentration was 0.0125 M EDOT and the electropolymerization time was 60 seconds

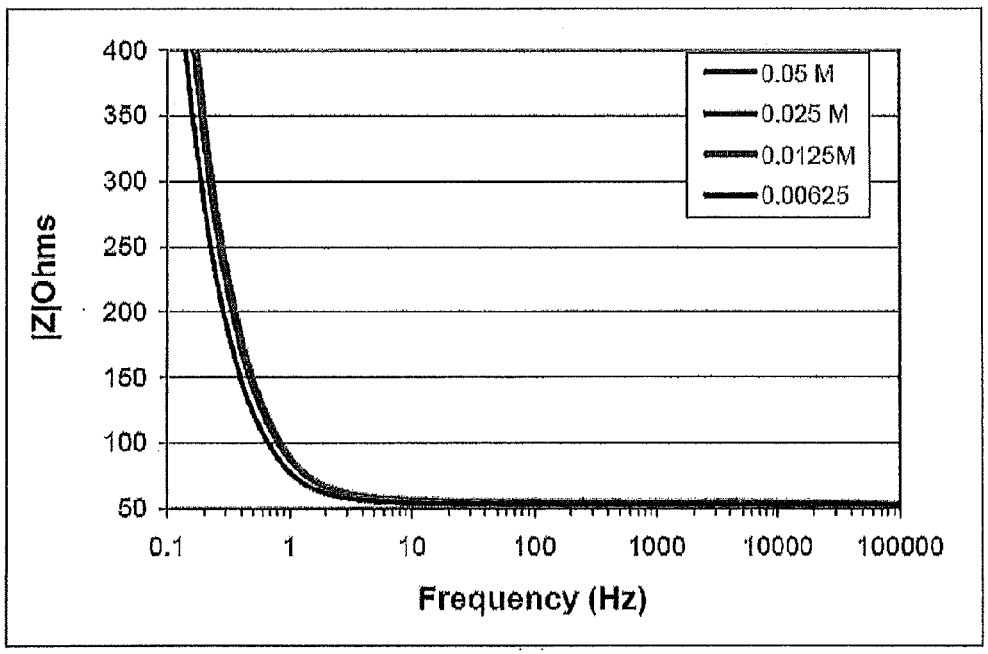

Figure 12: Bode plots for electrodes prepared with varying monomer concentrations. The counterion concentration during electropolymerization was 0.1 M $BF_4^-$ and electropolymerization occurred for 120 seconds.

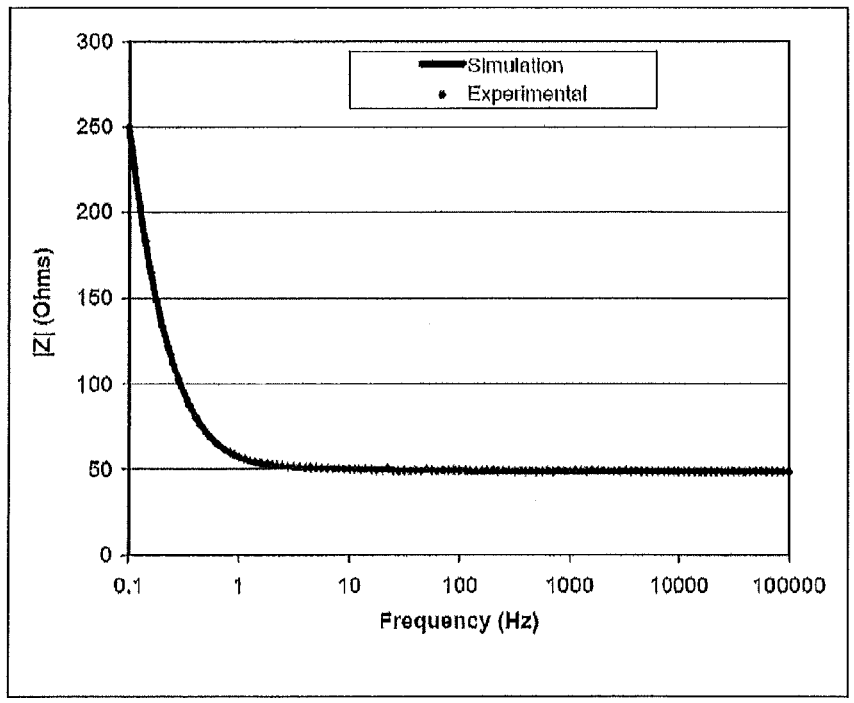

Figure 13. Comparison of theoretical behavior of circuit with that of an electrode produced using exemplary conditions: a) experimental; b) theoretical fit. Fitting parameters: $R_e$ = 1.459 Ohms ; $R_i$ = 49.09 ; CPE1 = 0.0065077 F; n = 0.98078 ; C1 = 1.978 x$10^{-9}$ F ; C = 0.0047423 F; X2 = 9 x$10^{-4}$

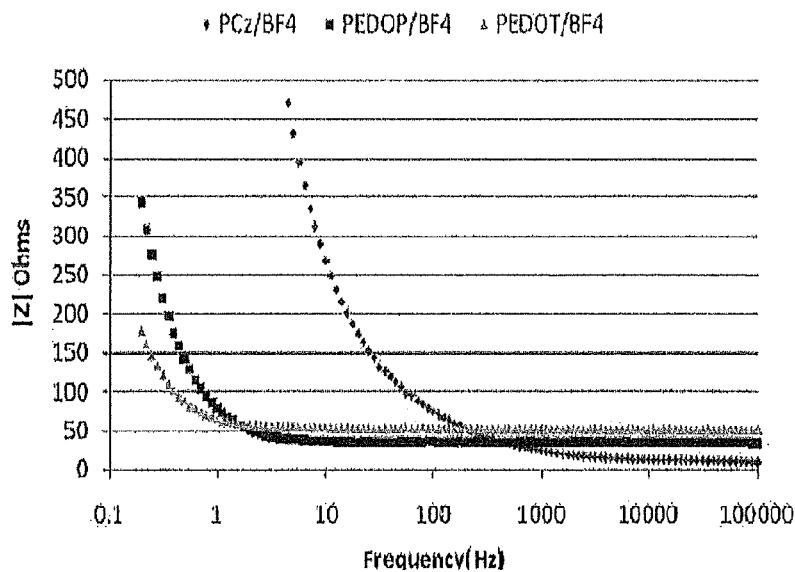

Figure 14: Bode plot from platinum electrodes modified with PEDOT, PEDOP and polycarbazole (each doped with $BF_4^-$)

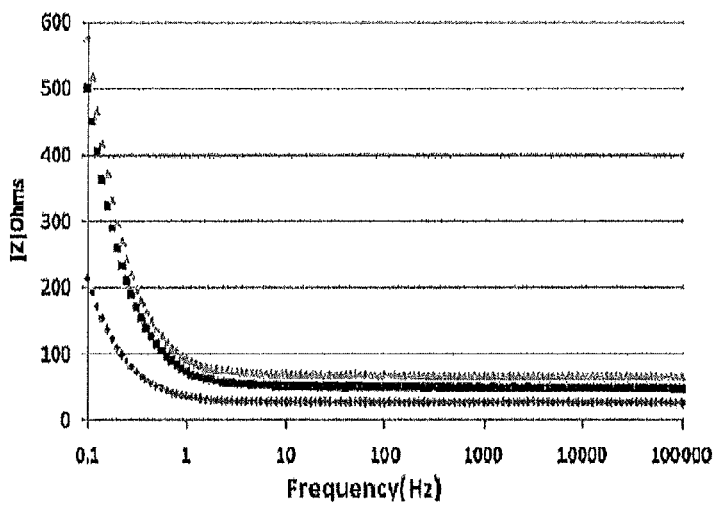

Figure 15: Comparision of PEDOT behavior after electropolymerization onto the different substrates. Electropolymerization Potential: 1300 mV vs. Ag/AgCl; EDOT: 0.0125 M in acetonitrile; Dopant: 0.1M $BF_4^-$ in acetonitrile; Electropolymerization time: 90 sec.

Solution conditions for EIS measurements: same as used in Figure 9

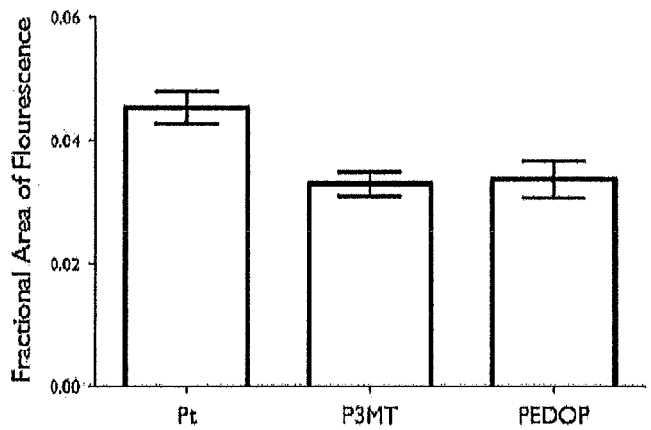

Figure 16: Tissue response to various electrodes, based on GFAP immunofluorescence

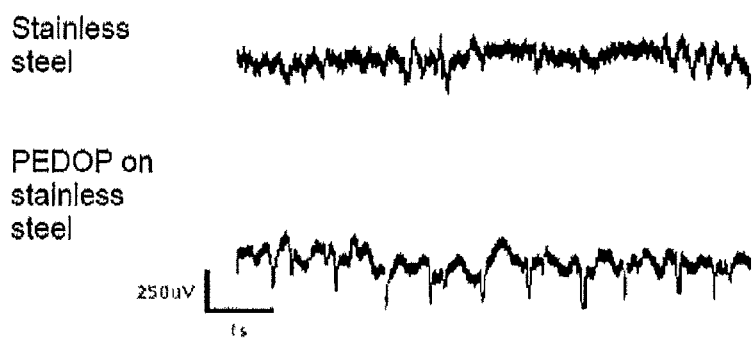

Figure 17: Measurement of seizure activity as detected at a conventional polyimide insulated stainless steel electrode compared to a PEDOP-modified stainless steel electrode. Seizure activity was induced using PTZ Electropolymerization conditions were as specified for the electrodes in Figure 12

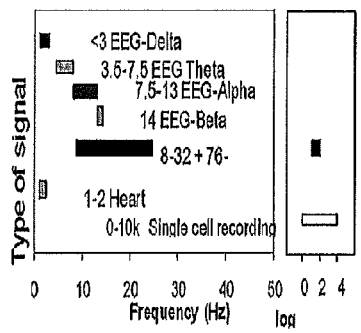

Figure 18. Typical biosignal frequency ranges
Gerard, M.; Chaubey, A.; Malhotra, B. D. "Application of conducting polymers to biosensors." *Biosensors and Bioelectronics*, 2002; 17, 345-35

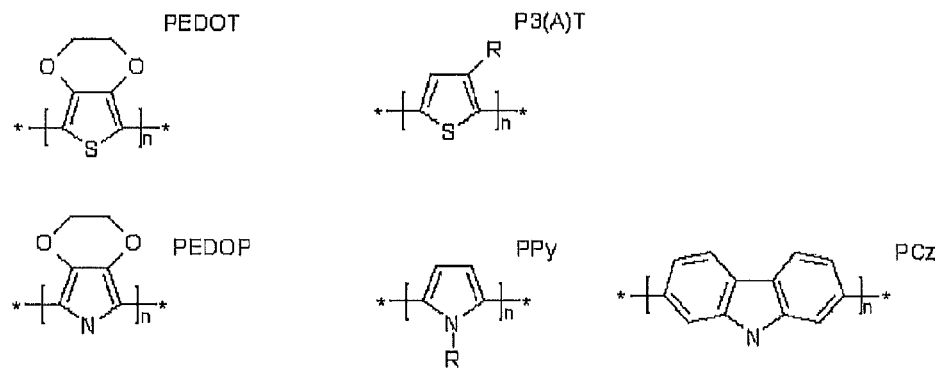
Figure 19. Structures of exemplary conducting polymers
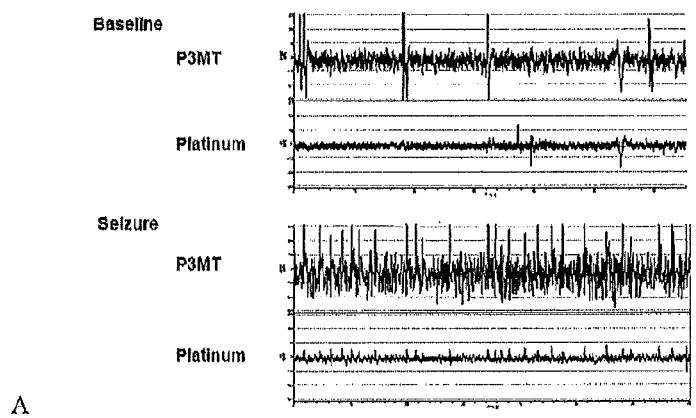
A
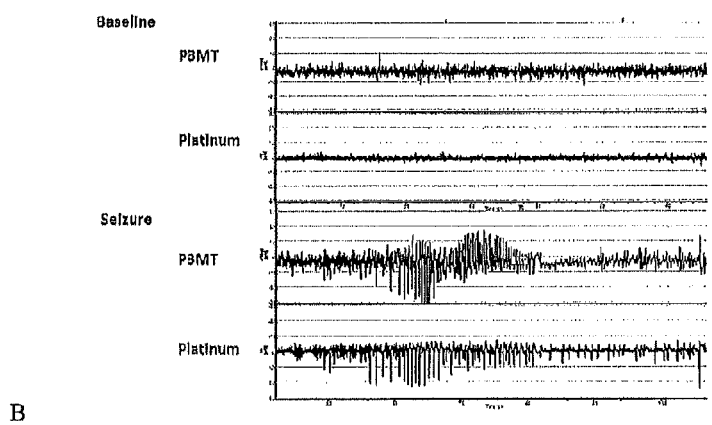
B

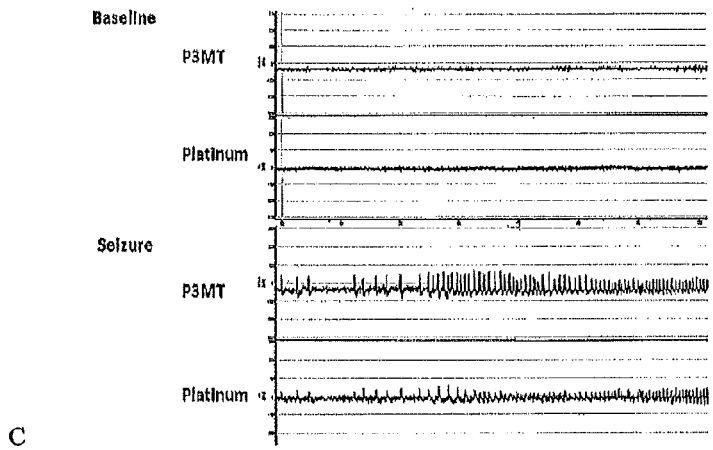

C

Figure 20. Displays the baseline and ictal platinum and P3MT recordings for Rat 1 (A), Rat 2 (B), Rat 3 (C)
 The x-axis represents the time scale in seconds and was cut down so that the data above represents a 70 second time frame
 The y-axis represents the potential readings of the electrodes at each second measured in microvolts (mV) and ranges from -300µV to 300µV

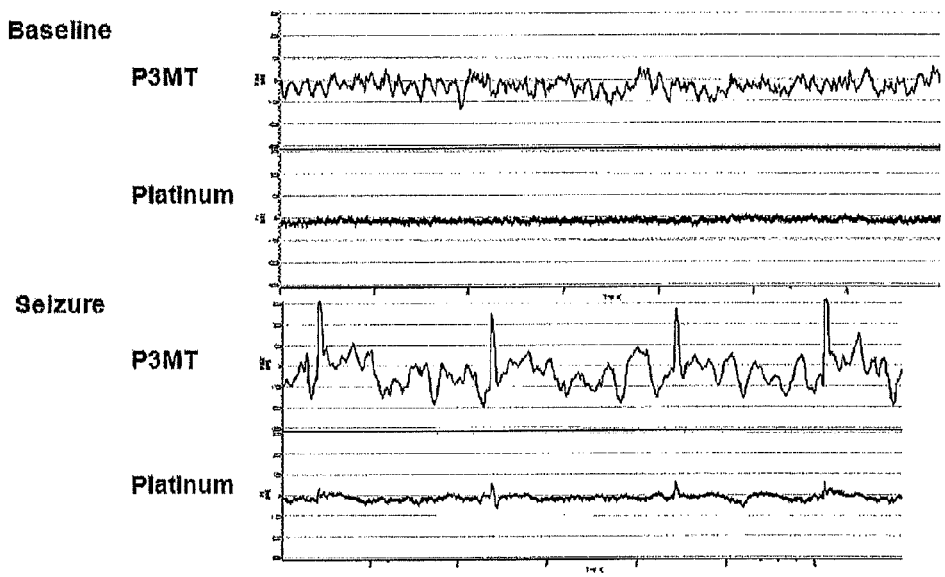

Figure 21. Displays the close up view of the baseline and ictal platinum and P3MT recordings for Rat 1 (A).
 X-axis represents the time scale in seconds and has a range of 8 seconds.
 The y-axis represents the potential readings of the electrodes at each second measured in microvolts (mV) and ranges from -300µV to 300µV.

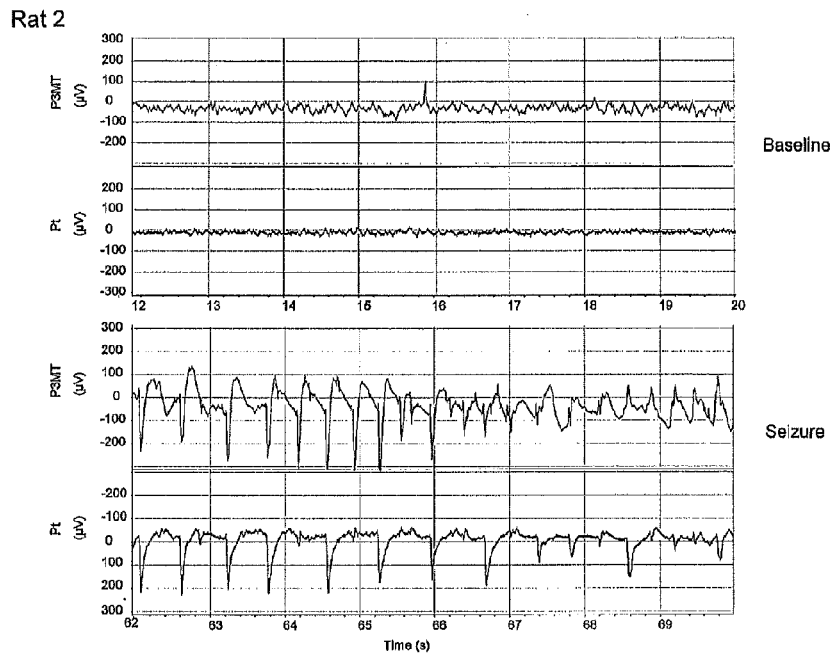
Figure 22. Displays the close up view of the baseline and ictal platinum and P3MT recordings for Rat 2 (B)
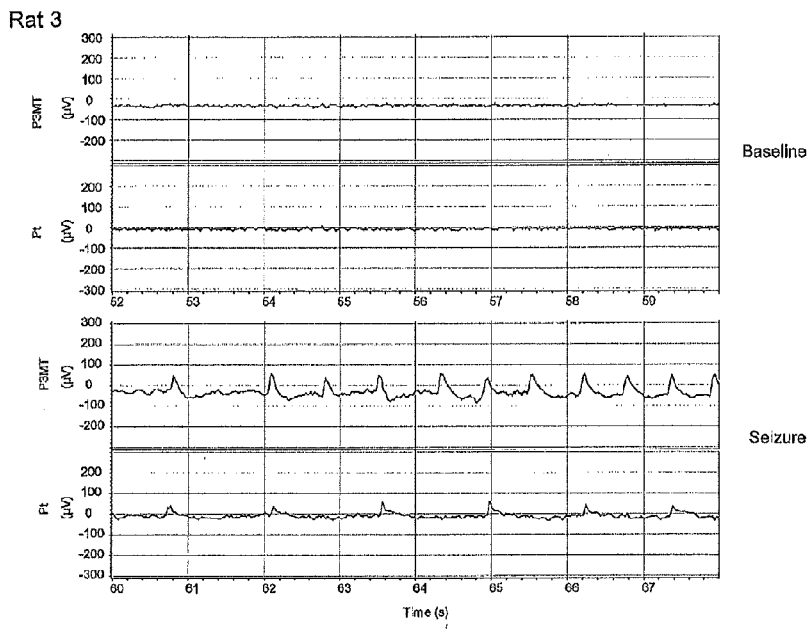
Figure 23. Displays the close up view of the baseline and ictal platinum and P3MT recordings for Rat 3 (C)

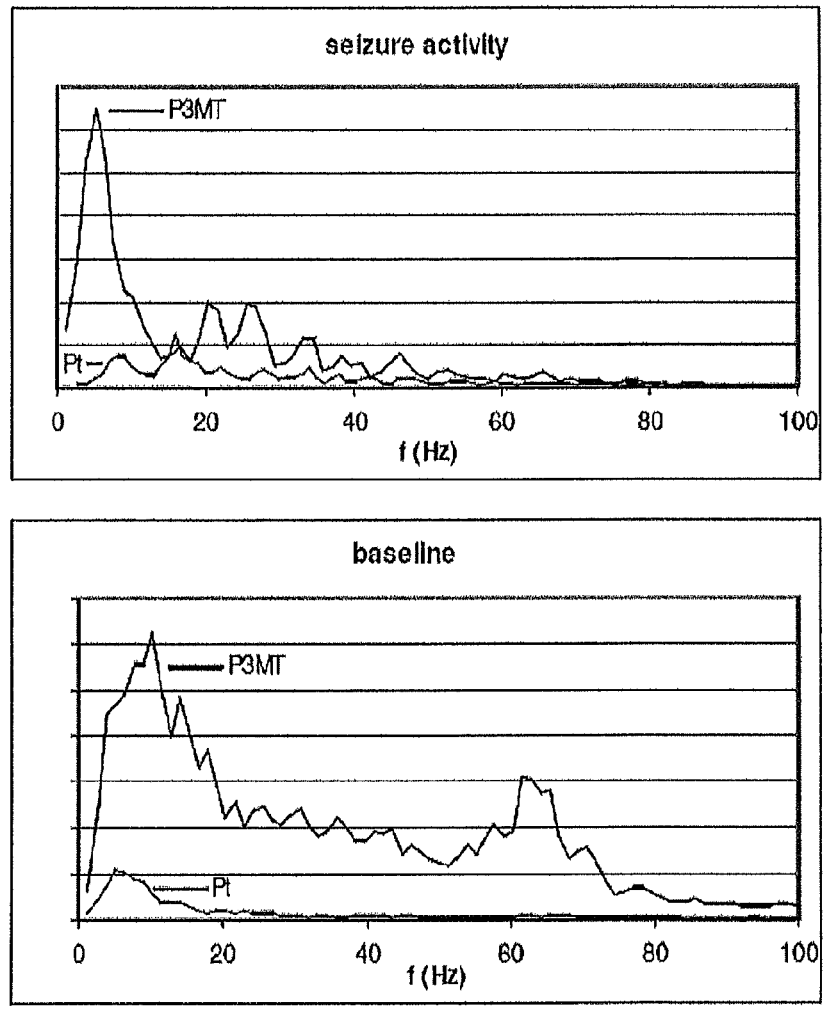
Figure 24. Comparison of signal throughput at f<100 Hz for P3MT vs Pt electrodes.

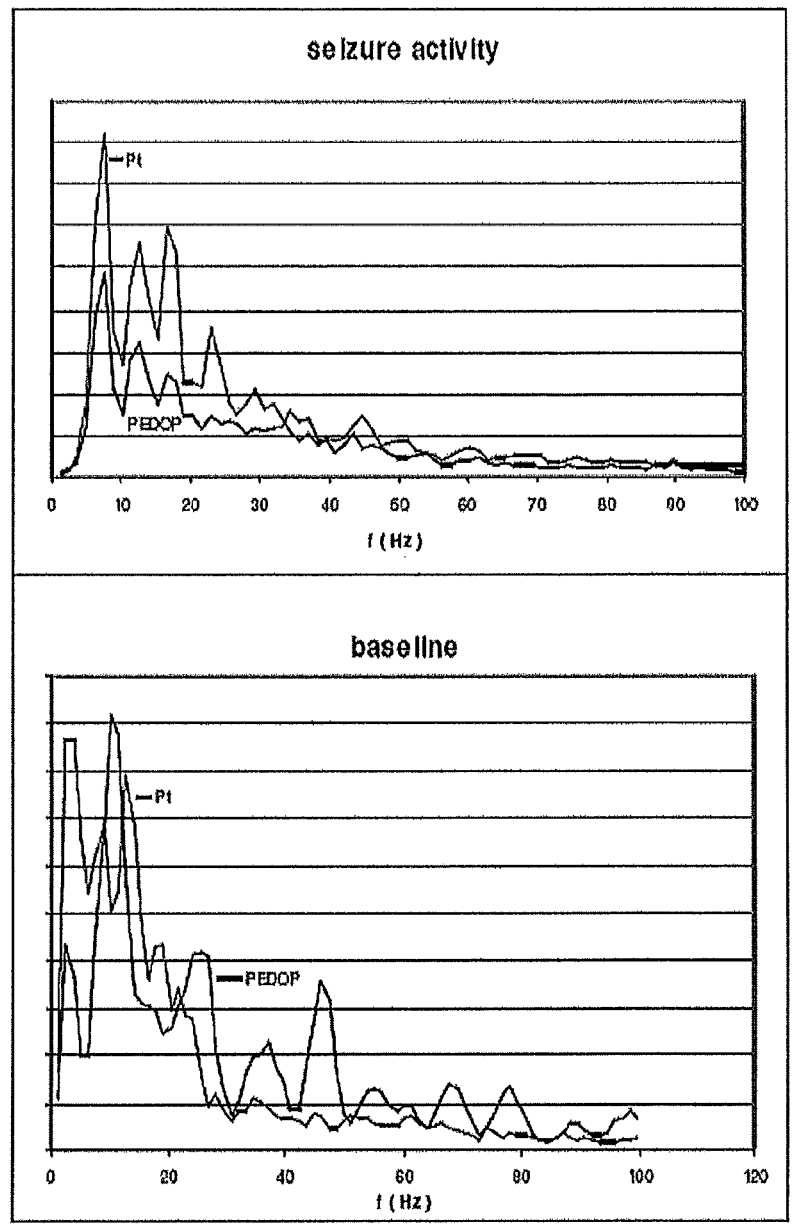
Figure 25. Comparison of signal throughput at f<100 Hz for PEDOP vs Pt

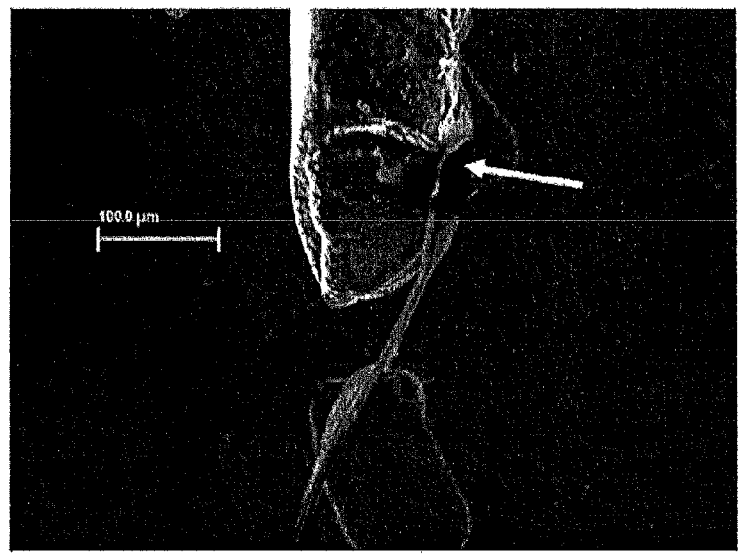
Figure 27: Poly-N-methylpyrrole fiber grown from the tip of a 100 μm Pt electrode at high flow rates
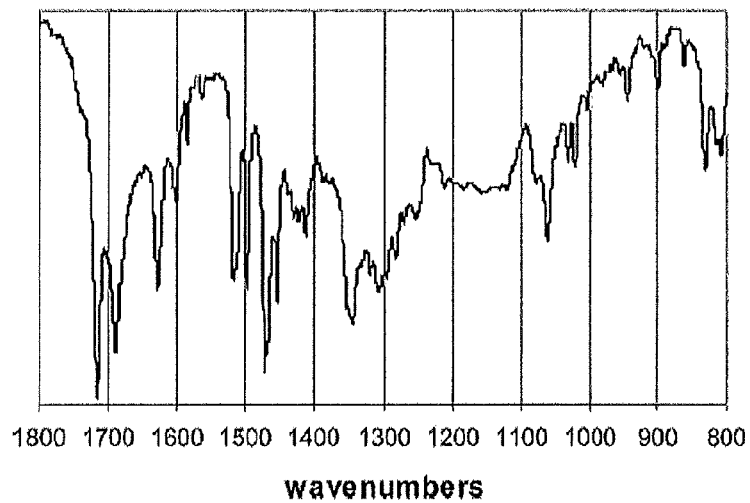
Figure 28: FTIR of a fiber of poly-N-methylpyrrole

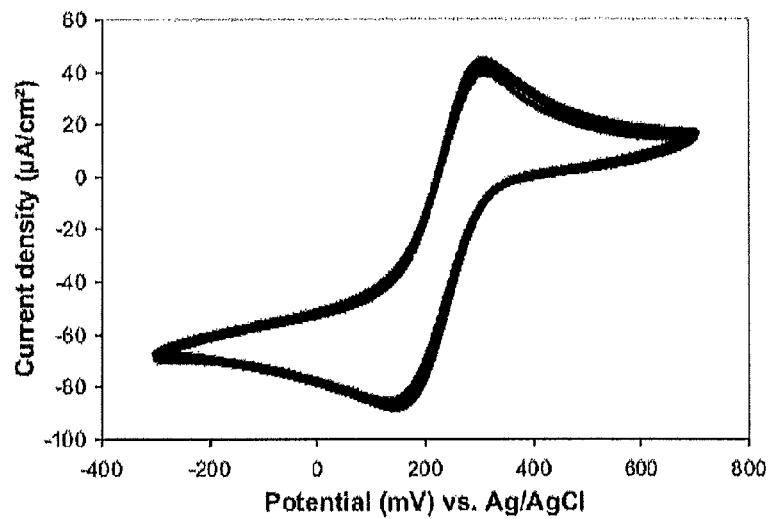
Figure 29: CV of 50 mM ferricyanide in 0.1 M KCl at the poly-*N*-methylpyrrole electrode
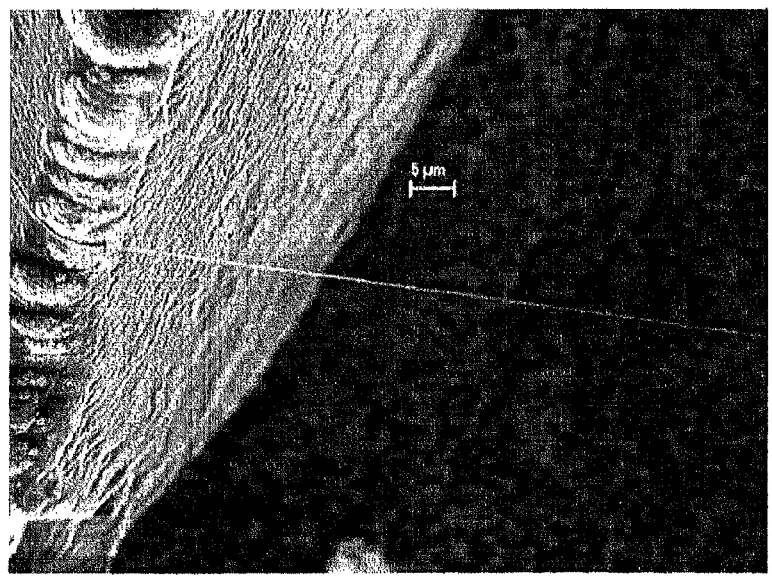
Figure 30: Poly-*N*-methylpyrrole fiber produced using conditions in Table II

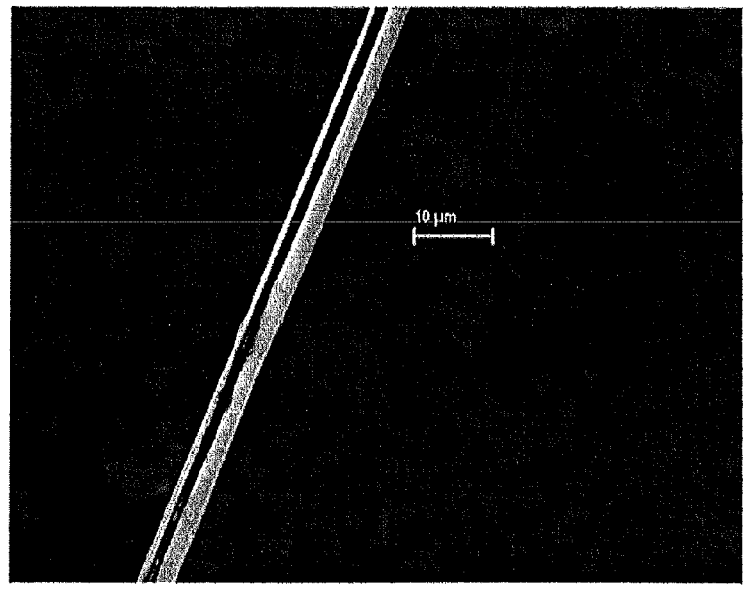
Figure 31: Poly-*N*-methylpyrrole fiber produced over a longer period of time using conditions in Table II
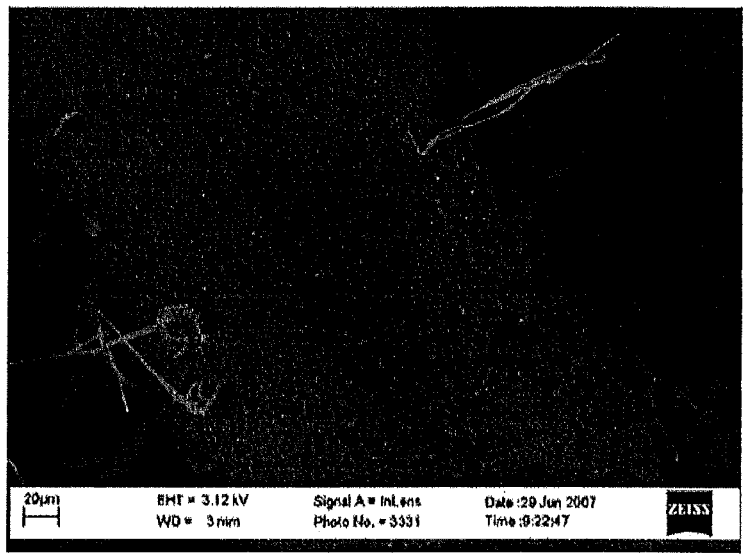
Figure 32: SEM of P3MT on Pt

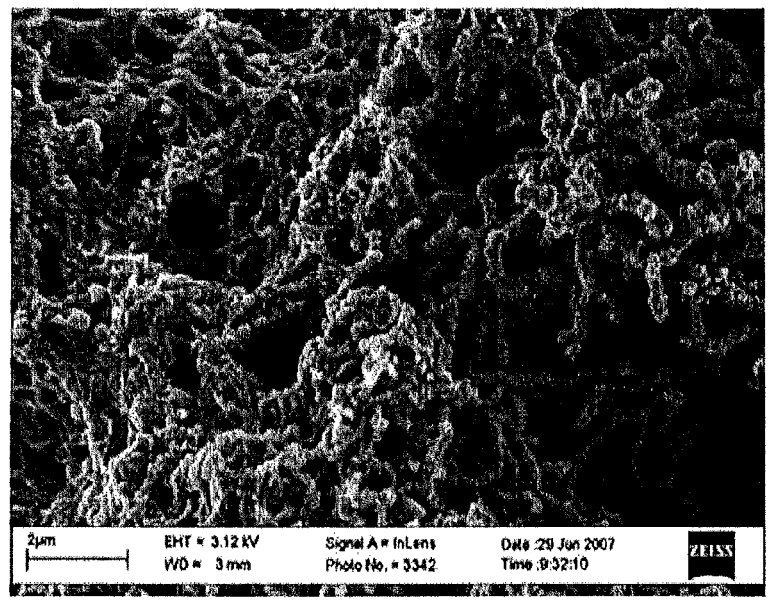
Figure 33: SEM of P3MT film having a thickness of about 100 μm resulting from an extended growth time
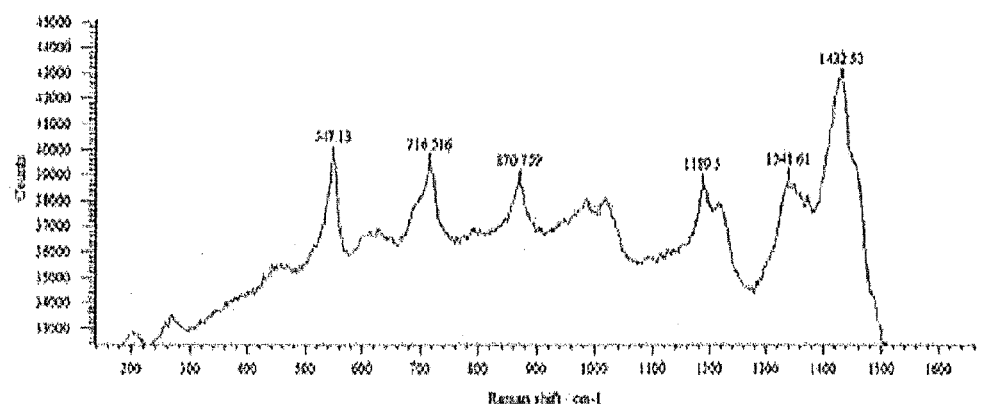
Figure 34: P3MT Raman spectra from a coating on a electrode

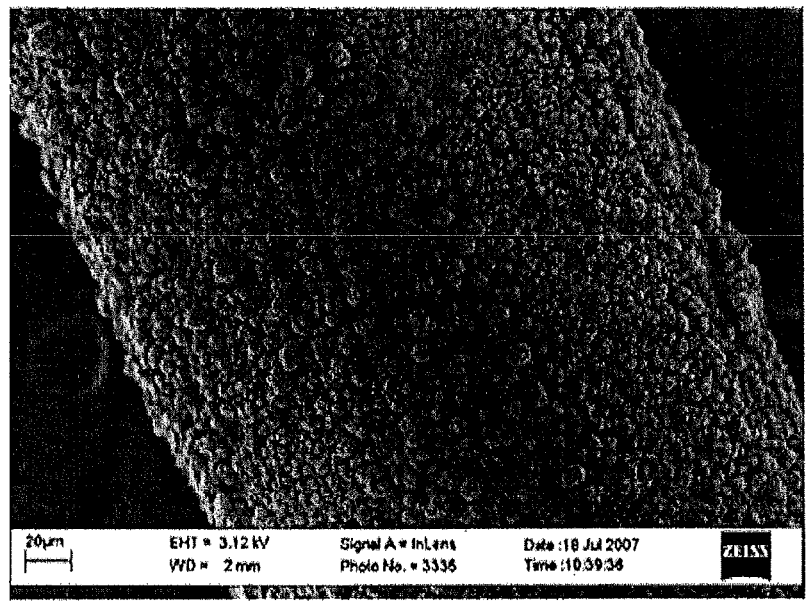
Figure 35: SEM of PEDOT on Pt
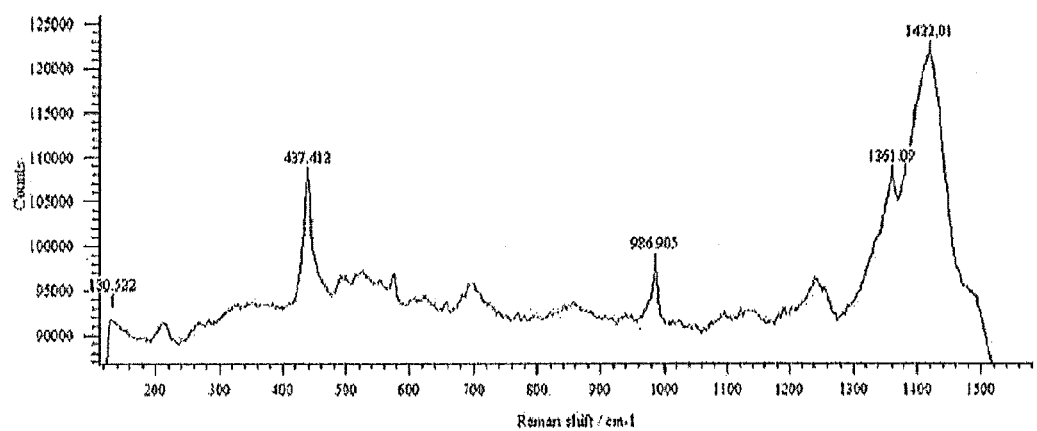
Figure 36: PEDOT Raman spectra from a coating on a electrode

POLYMER FILM BIOELECTRODES AND METHODS OF MAKING AND USING THE SAME

TECHNICAL FIELD

Polymer film electrodes, methods of making such electrodes and methods of using such electrodes for at least one of the detection, stimulation, and recording of electrical, chemical, and ionic interactions between a polymer film electrode and various biologic and chemical targets are described. Exemplary methods can be used for the detection and stimulation of charge transduction interactions between a conductive polymer and the surrounding tissue, cells, chemicals, electrolytes, charge carriers receptors and enzymes that are permitted to interact with the polymer film electrode.

"Conductive polymers" (also known as π-conjugated conductive polymers) are useful as biocompatible polymeric coating materials for electrodes, probes, and sensors. The use of conductive polymers can provide unique electrical and biochemical properties to these devices. The electrical properties imparted by the polymer constitute an improvement in the signal transmission and transduction properties. With regard to their interaction with tissue, these polymer electrodes address the issue that many materials currently used as electrodes in biomedical devices provide limited biocompatibility, which can result in tissue injury and inflammation in the vicinity of the implanted device. Such devices can also stimulate adverse tissue response and this response can lead to problems with the functioning of the device as well as result in potential health issues related to the tissue response.

BACKGROUND

Various bioelectrodes and related methods of making and using the same have been proposed. For at least the reasons provided below, conventional bioelectrodes and methods of making them are not optimal.

SUMMARY

This application relates to polymer film electrodes, methods of making such electrodes, devices that use such electrodes and methods of using such electrodes.

In an embodiment, the polymer film electrode comprises: (i) an electrically-conductive substrate; and (ii) an electrically-conductive polymer applied to the electrically-conductive substrate, wherein the electrically-conductive polymer is in electrical contact with the electrically-conductive substrate, and the electrode exhibits ohmic behavior over a range of at least one of (a) about 1 Hz to about 100 Hz and (b) about 800 Hz to about 100 kHz.

In an embodiment, the polymer film electrode comprises: (i) an electrically-conductive substrate; and (ii) an electrically-conductive polymer applied to the electrically-conductive substrate, wherein the electrically-conductive polymer is in electrical contact with the electrically-conductive substrate and the electrode has an impedance modulus of between about 1 ohm and about 75 ohms. ("Ohms," as used herein denotes the impedance modulus measured for an electrode comprising a polymer film deposited on a substrate of nominal surface approximately 0.17 $cm^2$). In other embodiments, the electrode has an impedance modulus over a range of from: (a) about 1 ohm to about 50 ohms, (b) about 5 ohms to about 40 ohms, (c) about 10 ohms to about 30 ohms, and (d) about 15 ohms to about 25 ohms.

In an embodiment, the method of manufacturing a polymer film electrode comprises: (i) preparing an electrically-conductive substrate; and (ii) applying an electrically-conductive polymer onto the electrically-conductive substrate, wherein the electrically-conductive polymer is in electrical contact with the electrically-conductive substrate and wherein the electrode exhibits ohmic behavior over a range of at least one of (a) about 5 Hz to about 100 Hz and (b) about 50 kHz to about 200 kHz.

In an embodiment, the method of manufacturing a polymer film electrode comprises: (i) preparing an electrically-conductive substrate; and (ii) applying an electrically-conductive polymer onto the electrically-conductive substrate, wherein the electrically-conductive polymer is in electrical contact with the electrically-conductive substrate and wherein the electrode has an impedance modulus of between about 1 ohm and about 75 ohms. In other embodiments, the electrode has an impedance modulus over a range of from: (a) about 1 ohm to about 50 ohms, (b) about 5 ohms to about 40 ohms, (c) about 10 ohms to about 30 ohms, and (d) about 15 ohms to about 25 ohms.

In an embodiment, a method of electrically detecting the transduction of electrical signals in a medium comprises the steps of: (a) providing a polymer film electrode comprising: (i) an electrically-conductive substrate; and (ii) an electrically-conductive polymer applied to the electrically-conductive substrate, wherein the electrically-conductive polymer is in electrical contact with the electrically-conductive substrate, and the electrode exhibits ohmic behavior over a range of at least one of about 1 Hz to about 100 Hz, and about 50 kHz to about 200 kHz; (b) placing the polymer film electrode in intimate contact with the medium; (c) electrically connecting the electrode and a second electrically-conductive substrate portion electrically coupled with the electrode to a instrument to detect the transduction of electrical signals; and (d) detecting the transduction of electrical signals with the electrode or stimulating and recording interactions in the medium around the electrode.

In an embodiment, a method of electrically detecting the transduction of electrical signals in a medium comprises the steps of: (a) providing a polymer film electrode comprising: (i) an electrically-conductive substrate; and (ii) a conductive polymer applied to the electrically-conductive substrate, wherein the conductive polymer is in electrical contact with the electrically-conductive substrate and the electrode has an impedance modulus of between about 1 ohm and about 75 ohms; (b) placing the polymer film electrode in intimate contact with the medium; (c) electrically connecting the electrode and a second electrically-conductive substrate portion electrically coupled with the electrode to an instrument to detect an electrical signal and (d) transduction of electrical signals with the electrode or stimulating and recording interactions in the medium around the electrode. In other embodiments, the electrode has an impedance modulus over a range of from: (a) about 1 ohm to about 50 ohms, (b) about 5 ohms to about 40 ohms, (c) about 10 ohms to about 30 ohms, and (d) about 15 ohms to about 25 ohms.

In an embodiment, a bioelectrode device comprises: a polymer film electrode and a biological component, wherein the polymer film electrode comprises: (i) an electrically-conductive substrate; and (ii) an electrically-conductive polymer applied to the electrically-conductive substrate, wherein (a) the electrically-conductive polymer is in electrical contact with the electrically-conductive substrate, (b) the electrode exhibits ohmic behavior over a range of about 1 Hz to about 100 kHz, (c) the polymer film electrode is electrically coupled to the biological component, and (d) the polymer film electrode transduces an electrical signal between the electrically-conductive substrate and the biological component.

In an embodiment, a bioelectrode device comprises: a polymer film electrode and a biological component, wherein the polymer film electrode comprises: (i) an electrically-conductive substrate; and (ii) an electrically-conductive polymer applied to the electrically-conductive substrate, wherein (a) the electrically-conductive polymer is in electrical contact with the electrically-conductive substrate, (b) the electrode has an impedance modulus of between about 1 ohm and about 75 ohms, (c) the polymer film electrode is electrically coupled to the biological component, and (d) the polymer film electrode transduces an electrical signal between the electrically-conductive substrate and the biological component. In other embodiments, the electrode has an impedance modulus over a range of from: (a) about 1 ohm to about 50 ohms, (b) about 5 ohms to about 40 ohms, (c) about 10 ohms to about 30 ohms, and (d) about 15 ohms to about 25 ohms.

In an embodiment, a method of electrically detecting a chemical or electrical signal between living cells, comprises the steps of: (A) providing a bioelectrode device and at least one biological component, the bioelectrode device comprising a first electrically-conductive substrate portion in intimate contact with tissue capable of charge transport, the bioelectrode device comprises: a polymer film electrode and a biological component, wherein the polymer film electrode comprises: (i) an electrically-conductive substrate and (ii) an electrically-conductive polymer applied to the electrically-conductive substrate, wherein (a) the electrically-conductive polymer is in electrical contact with the electrically-conductive substrate, (b) the electrode exhibits ohmic behavior over a range of about 5 Hz to about 200 kHz, (c) the polymer film electrode is electrically coupled to the biological component, and (d) the polymer film electrode transduces an electrical signal between the electrically-conductive substrate and the biological component, the bioelectrode transduces an electrical signal between the first electrically-conductive substrate portion and one of the biological component and conductive polymer; (B) electrically connecting the bioelectrode device and a second electrically-conductive substrate portion electrically coupled with the bioelectrode to a power source; (C) applying a voltage or current across the first and second electrically-conductive substrate portions, thereby inducing a voltage or current across the conductive polymer; and (D) detecting the transduction of electrical signals with the bioelectrode device.

In an embodiment, a method of electrically detecting a transduction of electrical signals between living cells, comprises the steps of: (A) providing a bioelectrode device and at least one biological component, the bioelectrode device comprising a first electrically-conductive substrate portion in intimate contact with tissue capable of charge transport, the bioelectrode device comprises: a polymer film electrode and a biological component, wherein the polymer film electrode comprises: (i) an electrically-conductive substrate and (ii) an electrically-conductive polymer applied to the electrically-conductive substrate, wherein (a) the electrically-conductive polymer is in electrical contact with the electrically-conductive substrate, (b) the electrode has an impedance modulus of between about 1 ohm and about 75 ohms, (c) the polymer film electrode is electrically coupled to the biological component, and (d) the polymer film electrode transduces an electrical signal between the electrically-conductive substrate and the biological component, the bioelectrode transduces an electrical signal between the first electrically conductive substrate portion and at least one of the biological component and conductive polymer; (B) electrically connecting the bioelectrode device and a second electrically-conductive substrate portion electrically coupled with the bioelectrode to a power source; (C) applying a voltage or current across the first and second electrically-conductive substrate portions, thereby inducing a voltage or current across the conductive polymer; and (D) detecting the transduction of electrical signals with the bioelectrode device. In other embodiments, the electrode has an impedance modulus over a range of from: (a) about 1 ohm to about 50 ohms, (b) about 5 ohms to about 40 ohms, (c) about 10 ohms to about 30 ohms, and (d) about 15 ohms to about 25 ohms.

In an embodiment, the polymer film electrode comprises: (i) an electrically-conductive substrate; and (ii) an electrically-conductive polymer applied to the electrically-conductive substrate, wherein the electrically-conductive polymer is in electrical contact with the electrically-conductive substrate and the electrically-conductive polymer is partially present as at least one continuous electrically-conductive polymer filament extending on the order of 100 microns or more from the polymer film electrically conductive substrate and having a uniform diameter of about 0.1 to about 1 micron for at least about 90% of its length.

In an embodiment, a method of manufacturing a polymer film electrode comprising an electrically-conductive substrate and an electrically-conductive polymer in electrical contact with the electrically-conductive substrate, where the electrically-conductive polymer comprises at least one fiber, comprises applying the electrically-conductive polymer onto the electrically-conductive substrate by electrodeposition of the electrically-conductive polymer from a solution of a monomer or oligomer used to form the electrically-conductive polymer and optionally at least one dopant, wherein the electrodepositing is conducted using a flow-through system having the solution flowing from the electrically-conductive substrate to a counterelectrode, wherein a deposition potential is present between the electrically-conductive substrate and the counterelectrode.

The applicability of the present teachings to other areas will become apparent from the detailed description provided hereinafter. It should be understood that the detailed description and specific examples, while indicating certain embodiments of the present teachings, are intended for purposes of illustration only and are not intended to limit the scope of the invention.

BRIEF DESCRIPTION OF THE DRAWINGS

FIG. 1 is a schematic of an exemplary embodiment of a polymer film electrode.

FIG. 2 is a morphological model of a poly(3,4-ethylenedioxythiophene, herein designated "PEDOT," film.

FIG. 3 shows a schematic of an embodiment of flow-cell setup for producing electrode having a fiber.

FIG. 4 is a cyclic voltammogram obtained from a PEDOT/$BF_4$ electrode.

FIG. 5 is a Raman spectra of PEDOT doped with various counterions.

FIG. 6 is a Bode plot from electrodes prepared with different counterions.

FIG. 7 is an SEM of the substrate/electrically-conductive polymer interface (a) and the surface of the electrically-conductive polymer (b and c) at different deposition times.

FIG. 9 is a diagram of a proposed equivalent circuit for a two layer morphology (PEDOT/BF$_4^-$ electrodes produced using exemplary conditions as described).

FIG. 10 is a Bode plot for electrodes prepared with varying electropolymerization times.

FIG. 11 is a Bode plot for electrodes prepared with varying TBABF$_4$ (tetrabutylammonium tetrafluoroborate) dopant concentrations.

FIG. 12 is a Bode plot for electrodes prepared with varying monomer or oligomer concentrations.

FIG. 13 shows a comparison of theoretical behavior of circuit with that of an electrode produced using exemplary conditions.

FIG. 14 is a Bode plot from platinum electrodes modified with PEDOT, poly(3,4-ethylenedioxypyrrole, "PEDOP," and polycarbazole (each doped with BF$_4^-$).

FIG. 15 is a comparison of PEDOT behavior after electropolymerization onto different substrates.

FIG. 16 shows the tissue response, based on GFAP immunofluorescence, from brains of rats receiving implants of various electrodes.

FIG. 17 shows electrical signals from the measurement of seizure activity as detected at a conventional polyimide insulated stainless steel electrode compared to a PEDOP-modified stainless steel electrode.

FIG. 18 shows the range of typical biosignal frequencies.

FIG. 19 shows the structures of exemplary conducting polymers.

FIG. 20 displays the baseline and ictal recordings from rats with platinum and P3MT electrodes.

FIG. 21 displays the close up view of the baseline and ictal platinum and P3MT recordings for Rat 1 (A).

FIG. 22 displays the close up view of the baseline and ictal platinum and P3MT recordings for Rat 2 (B).

FIG. 23 displays the close up view of the baseline and ictal platinum and P3MT recordings for Rat 3 (C).

FIG. 24 shows a comparison of signal throughput at f<100 Hz for P3MT vs Pt electrodes.

FIG. 25 shows a comparison of signal throughput at f<100 Hz for PEDOP vs Pt electrodes.

FIG. 27 shows a poly-N-methylpyrrole fiber grown from the tip of a 100 µm Pt electrode at high flow rates.

FIG. 28 shows the FTIR of a fiber of poly-N-methylpyrrole.

FIG. 29 shows a CV of 50 mM ferricyanide in 0.1 M KCl at the poly-N-methylpyrrole electrode.

FIG. 30 shows a poly-N-methylpyrrole fiber produced using a 15 minute deposition time.

FIG. 31 shows a poly-N-methylpyrrole fiber produced over a longer period of time using conditions in Table II.

FIG. 32 shows a SEM of P3MT on Pt.

FIG. 33 shows a SEM of P3MT film having a thickness of about 100 µm resulting from an extended growth time.

FIG. 34 shows a P3MT Raman spectra from a coating on a electrode.

FIG. 35 shows a SEM of PEDOT on Pt.

FIG. 36 shows a PEDOT Raman spectrum from a coating on an electrode.

DETAILED DESCRIPTION

Figure 8A:
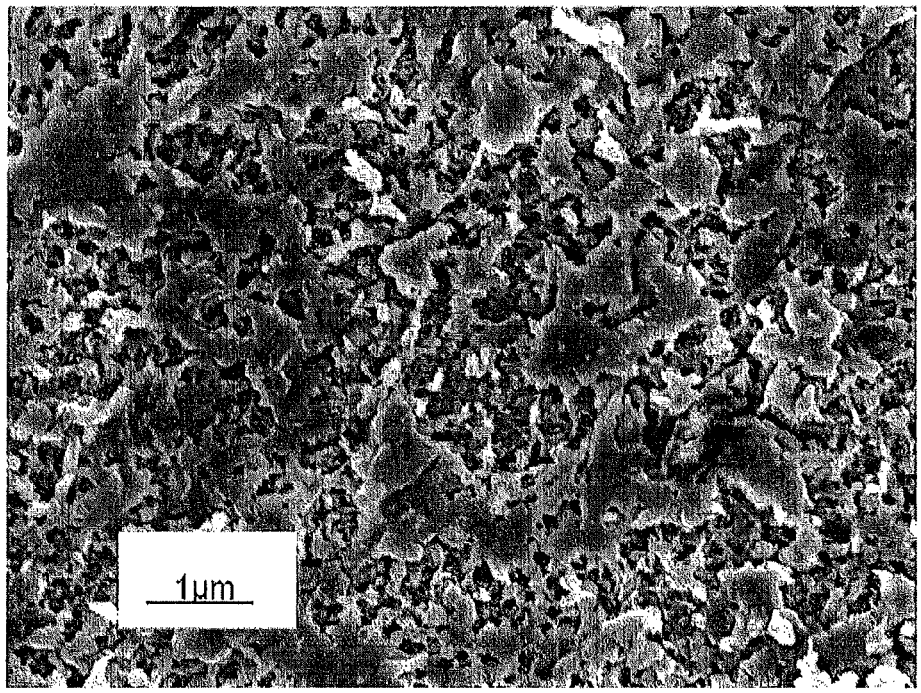
FIG. 8 contains SEM images showing morphology of PEDOT/BE$_4^-$ film formed after (a) 7, (b) 30, (c) 90, (d) 45 and 120 seconds at deposition potential.
FIG. 8(e) shows a cross section of PEDOT/BF$_4^-$.
FIG. 8(f) shows polymer morphology at the metal|polymer interface.
FIG. 8(g) shows surface morphology of PEDOT/PSS$^-$.

Exemplary polymer film electrodes include electrode devices that resist unwanted biodegradation, low electrical impedance, and long-term electrical stability under in vivo conditions. For example, in certain embodiments, the polymer film electrodes can be mechanically stable, able to resist undesired degradation, and maintain electrical integrity and connectivity for the duration of implantation.

It is to be understood that this application is not limited to particular embodiments described. It is also to be understood that the terminology used herein is for the purpose of describing particular embodiments only, and is not intended to be limiting, since the scope of the present application will be limited only by the appended claims.

Unless defined otherwise, all technical and scientific terms used herein have the same meaning as commonly understood by one of ordinary skill in the art. Although any methods and materials similar or equivalent to those described herein can also be used in the practice or testing of exemplary embodiments, specific preferred methods and materials are now described.

As used herein, the recitation of a numerical range for a variable is intended to convey that the variable can be equal to any of the values within that range. Thus, for a variable which is inherently discrete, the variable can be equal to any integer value in the numerical range, including the end-points of the range. Similarly, for a variable which is inherently continuous, the variable can be equal to any real or imaginary value of the numerical range, including the end-points of the range. As an example, a variable which is described as having values between 0 and 2, can be 0, 1 or 2 for variables which are inherently discrete, and can be 0.0, 0.1, 0.01, 0.001, or any other real or imaginary value for variables which are inherently continuous.

Definitions:

The following definitions are provided for specific terms which are used in the following written description.

As used herein, the singular form "a", "an" and "the" include plural references unless the context clearly dictates otherwise. For example, the term "a cell" includes a plurality of cells, including mixtures thereof.

As used herein, the term "about" means approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the term "in communication with" refers to the ability of a system or component of a system to receive an input from another system or component of a system and to provide an output response in response to the input.

As used herein, "a measurable response" refers to a response that differs significantly from background, as determined using controls appropriate for a given technique.

As used herein, the term "electrode" refers to a device that transduces an input to provide an electrical signal.

As used herein, the term "Bode plot" is a graph of the logarithm of the transfer function of a linear, time-invariant system versus frequency, plotted with a log-frequency axis, to show the system's frequency response.

As used herein, the term "Cyclic voltammetry" or "CV" is a type of potentiodynamic electrochemical measurement.

In a cyclic voltammetry experiment, the working electrode potential is ramped linearly versus time. When a set potential is reached, the electrode's potential ramp is inverted. This inversion can happen multiple times during a single experiment. The current at the working electrode is plotted versus the applied voltage to give the cyclic voltammogram trace. Cyclic voltammetry is generally used to study the electrochemical properties of an analyte in solution As used herein, the term "Electrochemical Impedance Spectroscopy" or "EIS" is a method of characterizing electrochemical systems. This technique measures the impedance of a system over a range of frequencies, and therefore the frequency response of the system, including the energy storage and dissipation properties, is revealed. The data obtained by EIS can be expressed graphically in a Bode plot. EIS can provide information about the energy storage and dissipation properties of almost any physico-chemical system, including electrochemical cells and biological tissue.

As used herein, the term "dopant," also called doping agent, means a material deliberately added to the conductive polymer for the purpose of modifying its electrical conductivity as a function of voltage and frequency.

As used herein, the term "frequency independent impedance" means that the phase angle is less than about 2° in the EIS data over the relevant range.

As used herein, the term "ohmic behavior" means that the value of the impedance is independent of the signal frequency over the range of interest.

As used herein, the term "work function" is defined as the minimum energy needed to remove an electron from the surface to a vacuum.

As used herein, the term "electrically-conductive substrate" is a material that is capable of conducting electricity onto which a conducting polymer is to be electropolymerized. A detailed description of an electrically-conductive substrate is provided below.

The detailed description of the present teachings provides information on polymer film electrodes, methods of fabricating such electrodes, and the use of such electrodes. Finally, the present teachings are exemplified with a number of polymer film electrodes and devices and experiments demonstrating the utility and novelty thereof. Reference is made to "Conductive electroactive polymers: intelligent polymer systems" by Gordon G. Wallace, et al., CRC Press, ISBN-10: 1420067095, (2008)

A. Electrode Components:

An exemplary electrode comprises an electrically-conductive substrate and an electrically-conductive polymer applied to said electrically-conductive substrate. FIG. 1 shows a schematic of an embodiment of an electrode. In this embodiment, the electrode comprises a housing, such as glass tubing, that contains an electrically-conductive material, such as a silver or copper wire. The wire is electrically joined to an electrically-conductive substrate, which partially extends from the housing. The nature of the elements comprising the electrode is described in detail below. In an embodiment, the wire is electrically connected to an electrically-conductive substrate with silver epoxy or solder. In an embodiment the electrically-conductive substrate is platinum wire. The portion of the housing from which the electrically-conductive substrate partially extends is sealed. In an embodiment, the seal comprises a non-conducting epoxy resin capable of binding the housing with the electrically-conductive substrate, such as a high vacuum epoxy sold by Varian under the trademark Torr-Seal®. FIG. 1*a* shows a portion of the electrode where the electrically-conductive substrate partially extends from the housing. An electrically-conductive polymer is applied to the electrically-conductive substrate and the electrically-conductive polymer is in electrical contact with the electrically-conductive substrate. FIG. 1*b* shows the portion of the electrode in an embodiment comprising an electrically-conductive substrate having a first electrically-conductive substrate portion and a second electrically-conductive substrate portion. The second electrically-conductive substrate portion is applied to the first electrically-conductive substrate portion and the second electrically-conductive substrate portion is in electrical contact with the first electrically-conductive substrate portion. An electrically-conductive polymer is applied to the second electrically-conductive substrate portion and the electrically-conductive polymer is in electrical contact with the second electrically-conductive substrate portion. The electrically-conductive polymer is electrically connected to the first electrically-conductive substrate portion through the second electrically-conductive substrate portion.

The electrically-conductive polymer can also be configured as shown in FIG. 2, where a compact layer (t) is adjacent to the electrically-conductive substrate and a porous layer (x) is present on the compact layer (t).

I. Electrically-Conductive Substrate:

The electrically-conductive substrate can comprise a conducting material or combination of conducting and non-conducting materials. The conducting material can be a metal, a non-metallic electrically-conductive substance, or a combination thereof. A number of exemplary electrically-conductive substrate configurations are described, and it is understood that other configurations can be used. In an embodiment, the electrically-conductive substrate comprises at least one material having a work function greater than the work function of the electrically-conductive polymer. In non-limiting embodiments, electrically-conductive substrates can be manufactured from at least one metal including, but not limited to: platinum, gold, iridium, palladium, tungsten, nickel, copper, aluminum, stainless steel, zinc, titanium, tungsten, and their alloys and oxides, such as indium-tin-oxide (ITO), combinations thereof and the like. One can also use one or more non-metallic electrically-conductive substances, such as carbon nano-wires, carbon fiber, glassy carbon, carbon composites, conductive ceramics, conductive monomer, oligomers or polymers, combinations thereof and the like.

In an embodiment, the electrically-conductive substrate comprises a first electrically-conductive substrate portion and a second electrically-conductive substrate portion, where the first electrically-conductive substrate portion is at least partially coated by the second electrically-conductive substrate portion.

In another embodiment, the second electrically-conductive substrate portion is comprised of a metal or a non-metallic electrically-conductive substrate, and the second electrically-conductive substrate portion is different from the first electrically-conductive substrate.

In another embodiment, the substrate comprises a first electrically-conductive substrate portion and a second electrically-conductive substrate portion, where the second electrically-conductive substrate portion is comprised of a metal or a non-metallic electrically-conductive substrate, and the second electrically-conductive substrate portion is different from the first electrically-conductive substrate portion and the first electrically-conductive substrate portion is at least partially coated by the second electrically-conductive substrate portion.

In a further embodiment, the second electrically-conductive substrate portion is comprised of at least one metal selected from the group consisting of platinum, gold, silver, iridium, palladium, tungsten, nickel, copper, aluminum, stainless steel, zinc, titanium, tungsten, an oxide thereof, an alloy thereof, combinations thereof, and the like.

In another embodiment, an electrically-conductive adhesion promoter can be present between the first electrically-conductive substrate portion and a second electrically-conductive substrate portion.

As used herein, the first electrically-conductive substrate portion is the material that is at least one of: in contact with, coupled to, and in communication with at least one electrical device. The second electrically-conductive substrate portion is in electrical contact with both the first electrically-conductive substrate portion and the electrically-conductive polymer.

In some embodiments, the electrode can be connected to other device components using at least one of wires, leads, conductive polymers, and other means that are in electrical communication with other device components used to at least one of to measure, record and analyze the voltage or flow of current across the electrode from the environment immediately around the polymer film electrode.

II. Electrically-Conductive Polymer:

As used herein, electrically-conductive polymers are conjugated polymers that are capable of conducting electrons through a conjugated system of carbon-carbon bonds in their oxidized or reduced state. The term "electrically-conductive polymers" is used interchangeably with "conducting polymer(s)," as described in the literature. Electrically-conductive polymers are formed from their monomer or oligomers via electrochemical polymerization, oxidative polymerization, and other methods commonly used in the art.

In some embodiments, the electrically-conductive polymer can include, but is not limited to, at least of one of the following polymers: poly(3,4-ethylenedioxythiophene) (PEDOT), a polypyrrole, a polyaniline, a polyacetylene, poly(diallyldimethylammonium chloride), poly-4-vinylpyridine, a poly(vinylalcohol), a polythiophene, a polymer blend thereof, combinations thereof and the like. The conductive polymer can comprise functionalized copolymers made, for example, from a substituted derivative of at least one or more of the above.

In some embodiments, the conducting polymers can include one or more of any non-conductive monomer or oligomer or polymer that can be made conductive in the presence of an appropriate source of dopant. In some embodiments, the electrically-conductive polymers described herein can also be chemically synthesized to contain one or more functional side groups that can allow for binding of various compounds, such as, for example, a protein, a lipid, and a nucleic acid, before, during or after formation of the conductive polymer. In some embodiments, the conductive polymer is biodegradable and will dissolve after some period of time in the presence of biological materials. For example, such degradation can occur when the electrode is implanted in situ. The biodegradable conducting polymer can include, but is not limited to, at least one of polypyrrole poly(3,4-ethylenedioxythiophene) block PEG, poly(3,4-ethylenedioxythiophene), tetramethacrylate, combinations thereof and the like, and/or others which are commercially available. In an embodiment, the conductive polymer has a compact layer that is not permeable to a solution adjacent to the electrode and the compact layer is a structure through which ionic motion is extremely slow/negligible and is overlaid with a structure that is ionically permeable, wherein the thickness of the compact layer and the porous layer together is less than about 10 microns.

III. Dopants:

Conductive polymers contemplated contain counter ions for polymerization and electroconductivity across an electrode-tissue interface. Electron delocalization is a consequence of the presence of conjugated double bonds in the conducting polymer backbone. To make the conducting polymers electrically-conductive, it is necessary to introduce mobile carriers into the double bonds, this is achieved by oxidation or reduction reactions and results in incorporation of counterions ("dopants") for charge balance, a process referred to as "doping." The concept of doping distinguishes conducting polymers from other kinds of polymers. In certain embodiments, the dopants—in this case, the anions of ionic electrolytes used to polymerize the electrically-conductive polymers—can include, but are not limited to, one or more of the following dopants, poly(styrene sulfonate) (PSS), $LiClO_4$, dodecylbenzene sulfonic acid (DBSA) or its sodium salt, p-toluenesulfonic acid (p-TSA), combinations thereof and the like.

In an embodiment, the conductive polymer is comprised of PEDOT and the dopant comprises tetrafluoroborate or perchlorate. In another embodiment, the electrically-conductive substrate comprises platinum, the second electrically-conductive substrate portion is comprised of gold and the conductive polymer is comprised of at least one member selected from the group consisting of polyalkoxythiophenes, polyalkylthiophenes, polyalkoxypyrroles, N-substituted polypyrroles, polycarbazole and N-substituted polycarbazoles, combinations thereof and the like.

The electrically-conductive polymers can impart desirable features that are not found in conventional electrode materials, such as platinum, iridium, indium tin oxide, tungsten, and silicon. For example, an exemplary polymer film electrode can be chemically and electrically stable over time following implantation in tissue, relatively non-biodegradable yet highly biocompatible, and/or elicit lower levels of negative tissue response when compared with conventional electrodes.

Manufacture of the Electrode:

In an exemplary embodiment, the method of manufacturing a polymer film electrode comprises: (i) preparing an electrically-conductive substrate; and (ii) applying a conductive polymer onto the electrically-conductive substrate, wherein the conductive polymer is in electrical contact with the electrically-conductive substrate and wherein the electrode exhibits ohmic behavior over a range of at least one of (a) about 5 Hz to about 100 Hz and (b) about 50 kHz to about 200 kHz. In another embodiment, the step of preparing the electrically-conductive substrate comprises: (i) fabricating the electrically-conductive substrate wire or planar disk electrode with an active surface defined by a diameter of about 5 to about 250 microns; and (ii) cleaning the electrically-conductive substrate electrochemically. In still another embodiment, the electrically-conductive substrate comprises a first electrically-conductive substrate portion and a second electrically-conductive substrate portion, and the electrically-conductive substrate is further prepared by coating the first electrically-conductive substrate portion with the second electrically-conductive substrate portion.

In an embodiment, the step of applying a conductive polymer onto the electrically-conductive substrate comprises electrodepositing the conductive polymer from a solution comprising a monomer or oligomer that forms the conductive polymer and an ionic dopant. Suitable monomers or oligomers one can use to produce exemplary electrically-conductive polymers, which are attached to the electrically-conductive substrate, can be present as micelles or dissolved in one or more appropriate solvents, e.g., one or more of: aqueous methanol, aqueous ethanol, acetonitrile, dimethyl formamide, acetone, dimethyl sulfoxide, combinations thereof, and the like, at an appropriate pH for the monomer or oligomer of interest, and at a temperature from about −10° C. to about 40° C. The electrically-conductive polymers can be deposited on the electrically-conductive substrate by a variety of means, preferably by electrodeposition. In an embodiment, the electropolymerization is conducted at a potential of about +500 mV to about +1800 mV relative to a silver/silver chloride electrode. In still another embodiment, the electropolymerization is conducted at a potential of about +1000 mV to about +1300 mV relative to a silver/silver chloride electrode. In a further embodiment, electrodepositing the conductive polymer onto the electrically conductive substrate comprises electropolymerizing a monomer or oligomer from a solution comprising an electrolyte, wherein the cation or anion of the electrolyte is a dopant in the polymer. In yet another embodiment, the solvent is a mixture of acetonitrile and water. In still another embodiment, the concentration of the monomer or oligomer in the solvent is about 0.05 M to about 0.5 M and the concentration of the dopant in the solvent is about 0.05 M to about 0.2 M. In a further embodiment, the concentration of the monomer or oligomer in the solvent is about 0.01 M and the concentration of the dopant in the solvent is about 0.1 M. In a further embodiment, the electropolymerization is carried out for a time of about 5 seconds to about 2 minutes. In another embodiment, the electropolymerization is conducted at a potential or a range of potentials which do not exceed the over-oxidation potential for the polymer as indicated by the presence of electroactive behavior to the extent that the electrode does not show ohmic behavior.

In an embodiment, a bioelectrode device comprises: a polymer film electrode and a biological component, wherein the polymer film electrode comprises: (i) an electrically-conductive substrate; and (ii) an electrically-conductive polymer applied to the electrically-conductive substrate, wherein (a) the electrically-conductive polymer is in electrical contact with the electrically-conductive substrate, (b) the electrode exhibits ohmic behavior over a range of about 1 Hz to about 100 kHz, (c) the polymer film electrode is electrically coupled to the biological component, and (d) the polymer film electrode transduces an electrical signal between the electrically-conductive substrate and the biological component. In another embodiment, the detecting step (d) comprises transduction of electrical signals from the biological component wherein the signal is at least one member selected from the group consisting of impedance, resistance, capacitance, inductance, and current, and combinations thereof. In a further embodiment, the bioelectrode further comprises one or more dopants.

In an embodiment, the biological component includes one or more of a tissue, organic living cell, a cellular constituent or combinations thereof. In another embodiment, the organic living cell is selected from the group consisting of natural eukaryotic cells, recombinant eukaryotic cells and prokaryotic cells and combinations thereof. In yet another embodiment, the cellular constituent is selected from the group consisting of a membrane, an organelle, an ion-channel, a lipid bi-layer, a receptor, an enzyme, a protein, an antibody, an antigen, a nucleic acid and combinations thereof. In still another embodiment, the eukaryotic cells are selected from the group consisting of cardiac cells, neural cells, muscle cells, stem cells, stromal cells, hematopoietic cells, combinations thereof and the like. In a further embodiment, the neural cells comprise neurons. In another embodiment, the bioelectrode further comprises at least one hydrogel in proximate contact with the conductive polymer.

In an embodiment, the polymer film electrode is of a size to be appropriate for the intended application selected from the group including (but not limited to) in vivo detection or stimulation of single cell events (about 0.1 to about 1 micron) or detection of stimulation of multiple cell events (about 1 to about 10 micron or an array of electrodes about 0.1 to about 1.0 micron in diameter). In another embodiment, the polymer film electrode is sized to fit within a biological cell. In yet another embodiment, the electrically-conductive substrate is in the form of a core, planar surface or ring.

Characteristics of the Polymer Film Electrodes:

In an exemplary embodiment, the electrode exhibits ohmic behavior over a range of at least one of (a) about 1 Hz to about 100 Hz and (b) about 800 Hz to about 100 kHz. In another embodiment, the electrode exhibits ohmic behavior over a range of about 10 Hz to about 100 Hz, either alone or in combination with other ranges. In yet another embodiment, the electrode exhibits ohmic behavior over at least one range selected from the group consisting of: (a) about 50 Hz to about 100 Hz, (b) about 10 Hz to about 100 Hz; (c) about 25 Hz to about 50 Hz, (d) about 10 Hz to about 50 Hz, (e) about 5 Hz to about 50 Hz, (f) about 10 Hz to about 25 Hz, (g) about 5 Hz to about 25 Hz, (h) about 1 Hz to about 25 Hz, (i) about 5 Hz to about 10 Hz, (j) about 1 Hz to about 10 Hz, (k) about 800 Hz to about 50 kHz, (l) about 800 Hz to about 25 kHz, and (m) about 800 Hz to about 10 kHz. In a further embodiment, the electrode exhibits ohmic behavior over at least one range selected from the group consisting of: (a) about 50 Hz to about 100 Hz, (b) about 10 Hz to about 100 Hz; (c) about 25 Hz to about 50 Hz, (d) about 10 Hz to about 50 Hz, (e) about 5 Hz to about 50 Hz, (f) about 10 Hz to about 25 Hz, (g) about 5 Hz to about 25 Hz, (h) about 1 Hz to about 25 Hz, (i) about 5 Hz to about 10 Hz, and (j) about 1 Hz to about 10 Hz, and exhibits ohmic behavior over at least one range selected from the group consisting of: (k) about 800 Hz to about 50 kHz, (l) about 800 Hz to about 25 kHz, and (m) about 800 Hz to about 10 kHz.

Exemplary polymer film electrodes can have low biodegradability, low electrical impedance, long-term electrical stability in aqueous solutions, and tunable softness/flexibility. Exemplary polymer film electrodes can be tailored to have a variety of surface morphologies (e.g., varying levels of order, porosity and roughness at the nanometer and/or micrometer scale). Indeed, exemplary electrodes can include any morphology exhibiting one or more of the advantageous properties described herein, such as low biodegradability, low electrical impedance, long-term electrical stability in aqueous solutions, softness/flexibility and ohmic behavior.

Methods of Manufacture of the Polymer Film Electrode:

In an embodiment, an electrode without the electrically-conductive polymer, shown in FIG. 1a, is placed in a solution of a monomer or oligomer, which, when polymerized, forms an electrically-conductive polymer. The solution of the monomer or oligomer can comprise at least one dopant. Polymerization of the monomer or oligomer can occur with electrodeposition of the electrically-conductive polymer onto an electrically-conductive substrate. When the electrically-conductive polymer is deposited onto an electrically-conductive substrate, various factors affect the nature of the electrode produced. A description of these factors is found below in Examples 1-6.

In an exemplary embodiment, a polymer film electrode comprises (i) an electrically-conductive substrate; and (ii) an electrically-conductive polymer applied to the electrically-conductive substrate, where the electrically-conductive polymer is in electrical contact with said electrically-conductive substrate and the electrically-conductive polymer is partially present as at least one continuous electrically-conductive polymer filament extending on the order of 100 microns or more from the electrically-conductive substrate and the filament has a uniform diameter of about 0.1 to about 1 micron for at least about 90% of its length. In another embodiment, the fiber does not exhibit any discernable surface features when analyzed by scanning electron microscopy at a resolution of about 0.1 micron. In yet another embodiment, the fibers are not subject to the formation of cracks or voids within one year of storage, as indicated by scanning electron microscopy analysis of the fiber. In an embodiment, the fiber body exhibits fluorescence of at least about 10 times that of the fluorescence levels upon excitation at 514.5 nm found for the polymer film deposited on the sides of the electrodes, when analyzed by microspectroscopy.

Exemplary electrically-conductive substrates and electrically-conductive polymers have been described above. In another embodiment, the electrically-conductive substrate comprises at least one material having a work function greater than the work function of the electrically-conductive polymer. In a further embodiment, the electrically-conductive substrate comprises a metal or a non-metallic electrically-conductive substrate. In yet another embodiment, the electrically-conductive substrate comprises at least one metal selected from the group consisting of platinum, gold, silver, iridium, palladium, tungsten, nickel, copper, aluminum, stainless steel, zinc, titanium, tungsten, an oxide thereof, an alloy thereof, combinations thereof, and the like. In still another embodiment, the electrically-conductive substrate comprises at least one member selected from the group consisting of a carbon nano-wire, a carbon fiber, a glassy carbon, a carbon composite, a conductive ceramic, a conductive monomer or oligomer, a conductive polymer, combinations thereof and the like. Especially suitable electrically-conductive substrates are Pt, stainless steel, and gold.

In an embodiment, the electrically-conductive substrate comprises a first electrically-conductive substrate portion and a second electrically-conductive substrate portion, wherein the first electrically-conductive substrate portion is at least partially coated by the second electrically-conductive substrate portion. In another embodiment, the second electrically-conductive substrate portion is comprised of a metal or a non-metallic electrically-conductive substrate and the second electrically-conductive substrate portion is different from the first electrically-conductive substrate portion. In yet another embodiment, the second electrically-conductive substrate portion is comprised of at least one metal selected from the group consisting of platinum, gold, silver, iridium, palladium, tungsten, nickel, copper, aluminum, stainless steel, zinc, titanium, tungsten, an oxide thereof, an alloy thereof, combinations thereof and the like.

In another embodiment, the conductive polymer comprises at least one member selected from the group consisting of PEDOT, a polypyrrole, a polyaniline, a poly(diallyldimethylammonium chloride), a poly-4-vinylpyridine, a poly(vinylalcohol) a polythiophene, a polymer blend thereof, combinations thereof and the like. Especially suitable electrically-conductive polymers include polypyrrole, poly(N-methylpyrrole), poly(3-methylthiophene), and poly (3,4-ethylenedioxythiophene). These electrically-conductive polymers can include one or more dopants, which have been described above. Especially suitable dopants include dodecylbenzene sulfonate, perchlorate, chloride, tetrafluoroborate, polymethylmethacrylate and combinations thereof. In an embodiment, the electrically-conductive polymer is poly-N-methylpyrrole, which is formed from N-methylpyrrole monomer or oligomer, and the dopant comprises dodecylbenzene sulfonate. Fibers formed from 3-methylthiophene monomer or oligomer with a dopant comprising dodecylbenzene sulfonate exhibited enhanced fluorescence when analyzed by microspectroscopy with excitation at 514.5 nm, compared to polymer film deposited on the sides of the electrodes.

The polymer film electrode comprising an electrically-conductive polymer that is partially present as at least one continuous, i.e., uninterrupted, electrically-conductive polymer filament is produced using a flow system to electrodeposit the electrically-conductive polymer onto the electrically-conductive substrate. FIG. 3 shows a schematic of an embodiment of flow-cell setup for producing an electrode having a fiber. A deposition cell was constructed that allowed for variation of parameters that affect the shape, diameter, and length of the fiber (or fibers) produced. These parameters included flow rate of the monomer or oligomer solution, diameter of the reaction region, diameter of the anode, concentration of the dopant in the monomer or oligomer solution, anode-cathode separation, deposition potential, and deposition time. Fibers were produced using both this cell under flow conditions and a conventional three electrode under quiescent solution conditions. The working electrodes (upon which the electrically-conductive polymer were deposited) were manufactured by soldering platinum wire to copper wire and sealing the connections inside of a glass pipette with an epoxy resin capable of binding the housing with the electrically-conductive substrate, such as a high vacuum epoxy sold by Varian under the trademark Torr-Seal®, so that only the platinum wire was exposed to the solution containing the monomer or oligomer to electrodeposit the electrically-conductive polymer. The portion of the platinum that would come into contact with the solder was coated with copper before the soldering process to prevent degradation of the connection. The auxiliary electrode was an about 500 µm platinum wire which was inserted through a septum. The substrate electrodes were cleaned by sonicating in a series of solutions (NaOH, $H_2SO_4$, hexane, and ethanol) before deposition to remove any surface dirt and oils before use. The working and counter electrodes were placed at each end of the apparatus. Potential was applied using an IBM model 225, Radiometer Voltalab 10, or Radiometer Voltalab 80 potentiostat in a two-electrode configuration, and current was monitored throughout the deposition. Working electrodes were also prepared using stainless steel and gold. Solutions recirculated in the apparatus contained the monomer or oligomer used to produce the electrically-conductive polymer. The monomer or oligomers used included pyrrole, N-methylpyrrole, 3-methylthiophene, and 3,4-ethylenedioxythiophene (EDOT). The solutions also included a dopant, such as dodecylbenzene sulfonate, perchlorate, chloride, tetrafluoroborate, and polymethylmethacrylate. A model QV2 FMI fluid-transduction pump was used to continuously recirculate monomer or oligomer solution through the cell.

The effect of the following parameters on film and fiber formation were evaluated: flow rate of the monomer or oligomer solution, diameter of the reaction region, diameter of the anode, concentration of the dopant in the monomer or oligomer solution, electrode separation, deposition potential and deposition time. The parameters which were held constant were the monomer or oligomer concentration (about 0.1 M) and diameter of counter electrode (about 0.5 mm). The films were deposited onto the working electrode in a standard cell by cyclic voltammetry (CV) cycling between about 0 and a potential below the overoxidation potential of the monomer or oligomer. In an embodiment, potential was cycled between about 0 and about 1800 mV. In an embodiment, the flow-rate of the solution past the end of the electrically-conductive substrate is in the region between laminar flow and turbulent flow, as defined by a Reynolds number of 1700-2000. In a further embodiment, the electrically-conductive substrate and the counterelectrode are separated by a distance of about 0.3 cm to about 7.0 cm. In yet another embodiment, the deposition potential is about 0.8 to about 1.3 V. In another embodiment, the solution flowing from the electrically-conductive substrate to the counterelectrode has a flow rate about 35 ml/min to about 120 ml/min. In still another embodiment, the electrically-conductive substrate has a diameter about 25 µm to about 250 µm. In a further embodiment, the dopant is present in the solution at a concentration of about 0.05 M to about 0.2 M. In yet another embodiment, the region between the electrically-conductive substrate and the counterelectrode has a diameter of about 2 mm to about 3 mm. In still another embodiment, the electrically-conductive polymer is poly-N-methylpyrrole, the flow rate is from about 35-120 ml/min, the electrode separation is about 3.5 cm to about 4.0 cm, the diameter of the working electrode is about 25 to about 250 µm, the region between the electrically-conductive substrate and the counterelectrode has a diameter of about 2 mm, the dopant is present in the monomer or oligomer solution at a concentration of about 0.05 M to about 0.2 M, and the deposition potential is from about 0.8 V to about 1.3 V. In a further embodiment, the flow-through system has the solution flowing from the electrically-conductive substrate to a counterelectrode wherein the flow is performed in a tubular region having a diameter of about 2 mm to about 3 mm. Exemplary parameters for the formation of a poly-N-methylpyrrole fiber are summarized in Table II.

TABLE II

Polymerization parameters used in the formation of a poly-N-methylpyrrole fiber:

| | |
|---|---|
| Reaction zone diameter | 2 mm |
| Working electrode | 0.1 mm Pt |
| Auxiliary electrode | 0.5 mm Pt |
| Deposition solution | aqueous 0.1M methylpyrrole + 0.1M NaDBS |
| Flow rate | 100 mL/min |
| Electrode separation | 3.5-4.0 cm |
| Deposition potential | 1.3 V |
| Deposition time | 15 min |

B. Methods of Use:

The polymer film electrodes can be used in electrode-based devices that can be used to detect, measure or control the electrical current or voltage in the system. Exemplary electrodes and electrode-based devices offer the ability to improve electrode performance in diverse electronic biomedical device applications, including, for example, cardiac pacemakers and defibrillators, biosensors and brain stimulators. In an embodiment, the system comprises at least one member selected from the group consisting of a living cell, tissue, a physiological fluid, a cell culture, and combinations thereof. The devices can include, or be connected to, controllers, analyzers, and other sensing devices and computers. These optional components can also be used to perform one or more of the following tasks: measure and record electrical events, current flow, resistance, conductance, capacitance, and potential of the integrated network or to perform electrical impedance spectroscopy or cyclic voltammetry. These analytical systems and devices are commercially available from numerous sources. Devices used with, or containing, the polymer film electrode can include, for example, power sources, actuators, and controllers for the delivery of current and/or voltage. Power sources can provide voltage potentials in either AC or DC current. In some embodiments, the polymer film electrode and electrode-based devices employing the polymer film electrode can be powered with batteries.

The polymer film electrode can be inserted/implanted in interstitial spaces in the tissue and in the extracellular matrix between cells, or can be inserted into a cell or collection of cells. The polymer film electrode is expected to trigger a negligible tissue response due to the nature of the electrically-conductive polymer and the size of the electrode. Exemplary electrode compositions described herein can replace those used in conventional biomedical devices intended for implantation in the body.

The present disclosure will be further understood with reference to the following non-limiting examples.

EXAMPLES

Example 1

Fabrication of Working Electrodes

Platinum (Puratronic grade) and silver (99.99%) wires, hydrogen tetrachloraurate(III), sulfuric acid, potassium chloride, potassium ferrocyanide, and acetonitrile (99.9%) The EDOT monomer or oligomer, 3,4-ethylenedioxythiophene, tetrabutylammonium tetrafluoroborate, tetrabutylammonium hexafluorophosphate, poly(sodium 4-styrenesulfonate) or PSS, sodium p-toluene sulfonate (TS) and lithium perchlorate (electrochemical grade), and acetonitrile, were purchased from commercial vendors. Acetonitrile was dried over 3 Å molecular sieve (Fisher Scientific) before use. All other chemicals were used without further purification. Adhesive polymer was obtained from Stan Rubenstein Associates (Foxboro, Mass.) or M.E. Taylor Engineering, Inc (Brookeville, Md.). Non-porous polymer (TorrSeal®) was purchased from Varian Vacuum, Inc. Aqueous solutions were prepared using 18.3 MΩ water produced with a Millipore RIOS purification system.

Electrodes were fabricated by attaching a 250 µm diameter×2 cm Pt wire to a 250 µm diameter×10 cm Ag wire via conductive silver epoxy or solder. The Ag/Pt junction area was housed in a short glass tube, approximately 8 cm long, and nonporous polymer was applied at the end of the glass tube where the working electrodes exits This avoids any liquid contact with the junction. The conductive epoxy and nonporous masking polymer were each allowed to cure for 24 hours before cleaning the protruding wire electrodes as described below. A diagram of such an electrode is show in FIG. 1a.

Each electrode was electrochemically cleaned in a solution which was purged with $N_2$ prior to, and blanketed with $N_2$ during, each step. All potentials are reported vs. Ag/AgCl. The cleaning sequence was as follows: −0.2 V in 5M NaOH for 15 minutes; 1.4 V for 10 minutes in 1 M $H_2SO_4$; 0.2 V for 30 seconds; twenty cycles between −0.2V to 1.2V in 1.0M $H_2SO_4$ at a scan rate of 100 mV/sec. The acid and base solutions were discarded after they were used to clean five electrodes and each electrode was rinsed with deionized H$_2$O before being placed in the next solution in the sequence.

A polycrystalline gold layer was then plated on the platinum wire by electrodeposition to improve film adhesion before deposition of the polymer. (Cui, X.; Martin, D.C. *Sensors and Actuators A: Physical* 2003, 103, 384-394) The plating process was allowed to run for 1 min—until approximately 100 mC (milli-Coulomb) had passed—at a constant potential of 0.3V vs. Ag/AgCl in 50 mM HAuCl$_4$ prepared in 0.1 M NaCl. The solution was discarded after every five electrodes and was deaerated with N$_2$ prior to, and blanketed with N$_2$, during, the plating process. A diagram of such an electrode with the gold layer is shown in FIG. 1b.

Electrodeposition and Electrochemical Characterization:

All electrochemical reactions were carried out in a one-compartment glass cell using a, three electrode cell configuration The reference and auxiliary electrodes were Ag/AgCl and platinum wire, respectively. All deposition and electrochemical characterization studies were performed using a Radiometer PGZ402 instrument controlled by VoltaMaster 4 software. No ohmic compensation was applied. EIS data shown herein were acquired at open circuit potential in 0.1 M KCl.

The PEDOT film was electrodeposited potentiostatically (1300 mV vs. Ag/AgCl) from an acetonitrile solution containing the EDOT monomer or oligomer and a background electrolyte, where the anion of the electrolyte is a dopant. Tetrabutylammonium tetrafluoroborate, tetrabutylammonium hexafluorophosphate, poly(sodium-4-styrenesulfonate), p-toluene sulfonate (TS) and lithium perchlorate were used as electrolytes, with tetrafluoroborate, hexafluorophosphate, p-toluene sulfonate and perchlorate, respectively, being incorporated as the chosen dopant. A diagram of such an electrode with polymer is show in FIG. 1c. Electropolymerization time varied between 30 seconds and 120 seconds to produce films of thickness 1.1-2.4 μm, as measured by SEM and/or inferred from charge transferred during deposition. The concentration of the monomer or oligomer (EDOT) and the identity and concentration of the background electrolyte were varied as described in the results sections below. The films were characterized using impedance spectroscopy, cyclic voltammetry, and Raman spectroscopy.

Cyclic voltammetry (CV) was used to investigate the stability of the films and to screen for the possibility of overoxidation of the films. Overoxidation has been reported to result in the production of sulfoxide moieties in the film and decreased conductivity and stability. (Dietrich, M.; Heinze, J.; Heywang, G.; Jonas, F. *Journal of Electroanalytical Chemistry* 1994, 369, 87-92; Zykwinska, A.; Domagala, W.; Pilawa, B.; Lapkowski, M. *Electrochimica Acta* 2005, 50, 1625-1633.) Electrodes prepared as described above exhibited reversible electrochemical behavior for ferricyanide before and after EIS experiments, thus providing evidence of stability during the EIS experiments. FIG. 4 shows a CV of PEDOT/BF$_4$ in 0.01 M Fe(CN)$_6^{4-}$/Fe(CN)$_6^{3-}$/0.1 M KCl produced under exemplary conditions, such as, for example, those discussed below. Voltammograms exhibited steady state behavior beginning with the second scan. (See FIG. 4) Two cathodic and two anodic peaks are observed. While the main (larger) peaks, separated by approximately 85 mV, can be attributed to the solution redox reaction of Fe(CN)$_6^{3-/4-}$ the origin of the shoulders on these peaks is unclear at this time. It is possible that these may derive from the redox reaction of Fe(CN)$_6^{3-/4-}$ which is adsorbed or incorporated as dopant at the inner pore walls during the CV testing. This ferri/ferrocyanide couple may be characterized by a potential which is slightly different from that in the bulk solution. This suggestion of an immobilized redox couple is supported by the nearly equal oxidation and reduction peak potentials. The second peak is absent in Fe(CN)$_6^{3-/4-}$ at a PEDOT/PSS-electrode (which, as reported below is almost pore-free), Fe(CN)$_6^{3-/4-}$ at Pt electrodes, and peaks do not appear in scans for PEDOT/BF4$^-$ in background electrolyte only. The capacitive current background may be attributed to double layer charging. (Eliseeva, S.; Spiridonova, D.; Tolstopyatova, E.; Kondratiev, V. *Russian Journal of Electrochemistry* 2008, 44, 894-900) Stability of the film was verified by monitoring the charge transduction during the anodic and cathodic processes for the electrode in the background electrolyte, and no decrease was observed.

Raman spectroscopy was used to estimate the doping level achieved within the films, employing a Renishaw Ramascope instrument interfaced to an Olympus BH-2 microscope and equipped with a 25 mW 785 nm laser a Rayleigh filter, and a 1200 line/mm grating. Peak areas used for determination of doping level were based on the deconvoluted areas. Spectra were acquired under ambient conditions on samples prepared in the same manner as described for the working electrodes used for the EIS studies. All electrodes investigated show structural vibration modes typical for PEDOT, as seen in FIG. 5. The maximum of the C$_\alpha$=C$_\beta$ absorption band resulting from the doped, oxidized polymer is located at approximately 1432 cm$^{-1}$. The shoulder which appears at approximately 1412 cm$^{-1}$ has been assigned to the asymmetric vibration of C$_\alpha$=C$_\beta$ associated with the neutral (reduced) form. The integrated intensity ratio of these peaks (I=/$_{1412cm-1}$/I$_{1432cm-1}$) was used to estimate the doping level, y, based on the equation developed by Chiu, et al:

$$I = 0.087y - 2.279. \quad (1)$$

where / is the natural logarithm of the peak ratio. (Chiu, W.; Travas-Sedjic, J.; Cooney, R.; Bowmaker, G. *J Raman Spec* 2006, 37, 1354-1361)

The doping levels of the PEDOT polymers with the ions are tabulated in Table 1. BF$_4^-$ leads to the highest doping level while PSS" leads to the lowest.

TABLE 1

Doping level of PEDOT polymers in this study

| Counterion | | Estimated doping level (based on equation 1) |
|---|---|---|
| Tetrafluoroborate | BF$_4^-$ | 35.2 |
| Hexafluorophosphate | PF$_6^-$ | 31.6 |
| Perchlorate | ClO$_4^-$ | 31.3 |
| p-toluene sulfonate | Ts$^-$ | 28.4 |
| Polystyrene sulfonate | PSS$^-$ | 26.1 |

All values were in the normal range of one dopant for every three or four sites (Chiu, W. W.; Travas-Sejdic, J.; Cooney, R. P.; Bowmaker, G. A. *Synthetic Metals* 2005, 155, 80-88) and none of the polymers exhibit an S=O stretch at approximately 1320 cm$^{-1}$ which would be characteristic of sulfoxide groups present in the overoxidized form (Casado, J.; Zotti, G.; Berlin, A.; Hernandez, V.; Ortiz, R.; Navarrete, J. *J Molec Structure* 2005, 744-747, 551-556). The low impedances (described below), the typical doping levels, and the absence of an S=O vibration in the Raman suggest that the polymers produced using the methods described are not overoxidized.

The electrodes were characterized by EIS. FIG. 6 shows Bode plots obtained for PEDOT electrodes doped with $ClO_4$, $PSS^-$, $BF_4^-$, $TS^-$ or $PF_6$. PEDOT/$PSS^-$ and PEDOT/$TS^-$ electrodes exhibited the highest frequency-dependent impedance at frequencies below 1 kHz. Though the impedances of PEDOT doped with the other inorganic anions are comparable in magnitude, PEDOT/$BF_4^-$ is distinguished from the other electrodes by slightly lower impedance magnitude and frequency-independent behavior over a broader ranger of frequency. The impedances of the other three electrodes are comparable in magnitude. PEDOT electrodes prepared as described above with $ClO_4$, $BF_4$, or $PF_6$ exhibit near ohmic behavior at frequencies of 5 Hz or less. (See insert in FIG. 6) The range over which the impedance was frequency independent for the PEDOT/$BF_4$ electrodes was a function of electrodeposition parameters. A typical batch of ten electrodes, when fabricated using the optimal conditions, exhibited constant, almost resistive impedances (phase angle <about ±2°) over the frequency range which extended from about 5 Hz on the lower end to an upper limit of about 200 kHz.

In general, PEDOT films prepared as described above with smaller anionic background electrolytes than $PSS^-$, or even its monomer or oligomer p-toluene sulfonate, exhibit near ohmic behavior at frequencies <1000 Hz, in particular below 10 Hz, which is unusual for polymer-modified electrodes.

The range over which the impedance was frequency-independent for the PEDOT/$BF_4^-$ electrodes was, as noted below, sensitive to electrodeposition parameters. However, when fabricated using the optimal conditions, the high frequency impedance modulus of 50 ohms, as measured by EIS □ (a function of the IR drop across the Ag/AgCl reference electrode and the solution resistance during the EIS measurements) and the low frequency cutoff for constant, non-frequency dependent impedance (phase angle <±2°) were both consistent electrode-to-electrode. The optimization is robust.

Equivalent Circuit Consistent with Behavior:

It is generally agreed that the external surfaces of conducting polymer films are porous. This follows from their growth mechanism, which involves a 2D nucleation growth followed by a 3D growth. (Kemp, N. T.; Cochrane, J. W.; Newbury, R. *Synthetic Metals* 2009, 159, 435-444 and Soto, J. P.; Diaz, F. R.; del Valle, M. A.; Vélez, J. H.; East, G. A. *Applied Surface Science* 2008, 254, 3489-3496. The initial 2D nucleation growth results in a complete coverage of the substrate by a homogeneously compact layer. Subsequent growth leads into the formation of a porous, non-compact layer on the top of the compact layer. (Kupila, E.-L.; Kankare, J. *Synthetic Metals* 1995, 74, 241-249). Solvent, counterion type, and deposition rate affect the morphology and the quality of the film (See Kupila), as all of these impact the kinetics of these growth steps.

SEM Characterization:

Samples of polymer modified wires (prepared using same manner as described below for the working electrodes used for the EIS studies) were cut and placed onto circular adhesive carbon films for affixing to aluminum sample stubs. The electron micrographs were collected using a Zeiss Ultra Plus Field Emission scanning electron microscope with an operating voltage range of 1-5 kV. All images were captured using the software SmartSEM Ultra Plus under ultrahigh vacuum conditions.

SEM images of the polymer morphology from a PEDOT/$BF_4^-$ film removed from a Pt substrate on an electrode is show in FIG. 7. The scale mark in the figure is 1 micron).

FIG. 7A shows the polymer morphology at the interface between the electrically-conductive polymer and the Pt substrate which was formed after a deposition time of about 90 sec. This scan shows the "backside" of the film after removal from the Pt substrate. The dark sections are areas where gold came away from the surface of the substrate. FIGS. 7B and 7C show the external morphology of film after a deposition time of about 30 seconds, and about 90 seconds, respectively. The images were acquired normal to the polymer film surface.

Figure 8B:
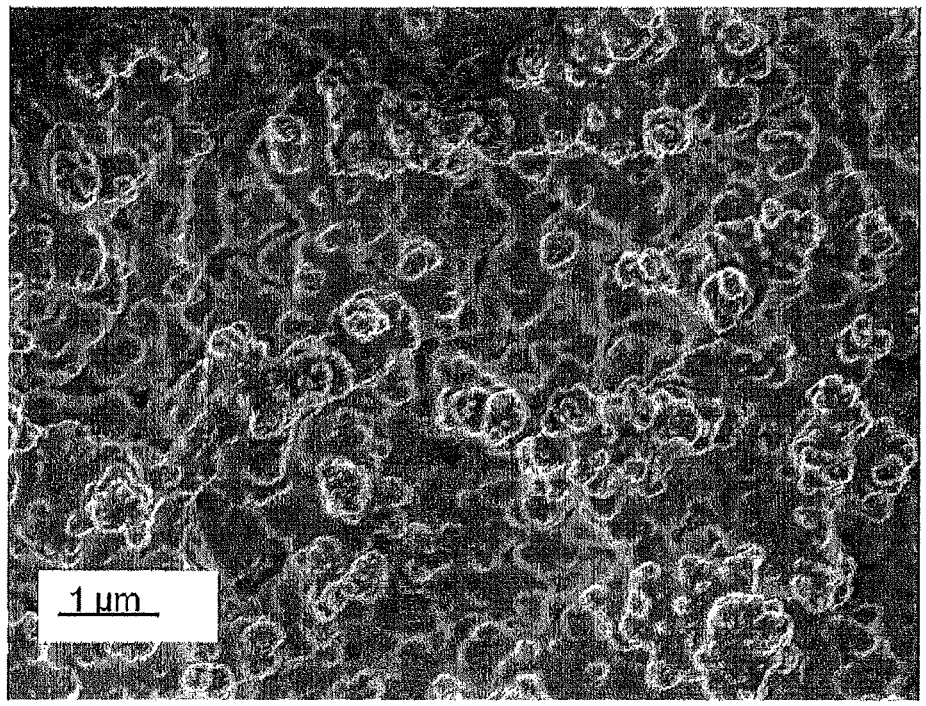
Figure 8C:
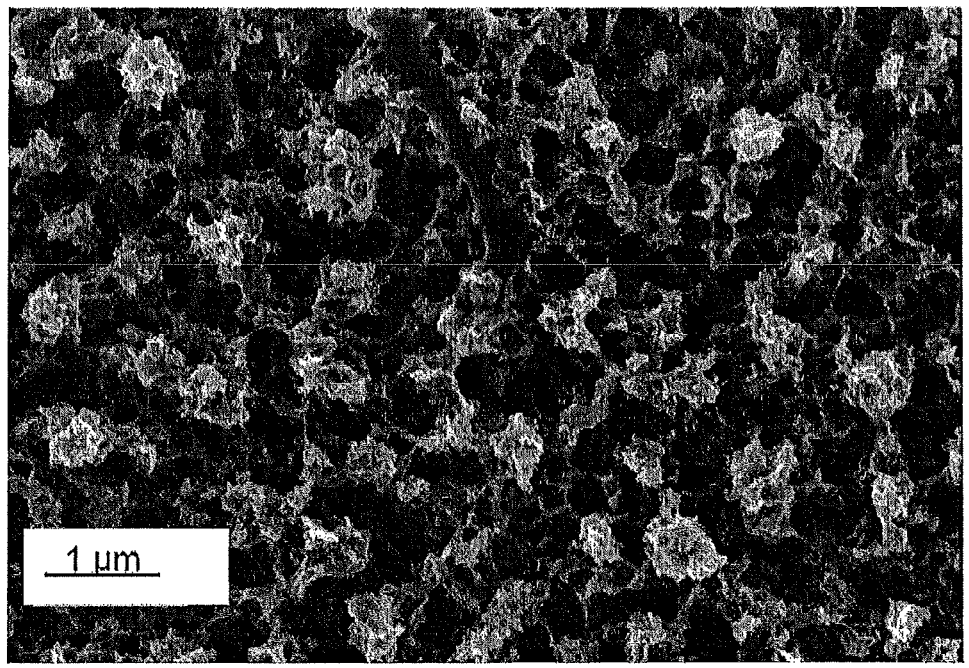

Morphology Studies by SEM:

SEM images (FIGS. 8*a-g*) provide concrete evidence for the proposed morphological model. FIGS. 8*a-d* show the surfaces of a series of electrodes prepared using difference electrodeposition times. In FIG. 8*a*, the early stages of nucleation (7 seconds) can be seen, while FIG. 8*b* shows the outer surface of the film after electropolymerization for 30 seconds. It is obvious that initial nucleation sites coalesce to form a dense, compact film. The 30-second electrode exhibits a more compact structure and a smoother morphology compared to that of a film produced over a 90 second electropolymerization period (FIG. 8*c*).

Figure 8D:
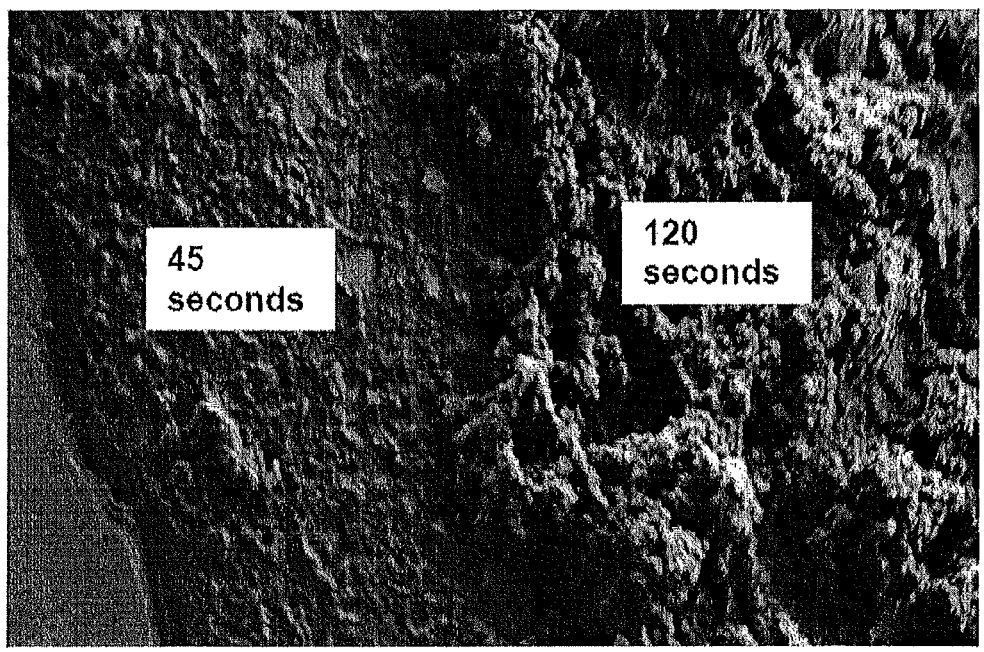

The increase in film porosity with increasing thickness is also illustrated in FIG. 8*d*. The film was produced by partially immersing the wire in the electropolymerization solution and raising a part of it above the solution after 45 seconds. The bottom portion of the electrode was left in the solution to allow additional polymerization for 75 seconds. The portion formed at longer polymerization times was much more porous at its outer surface and the structure appeared to be more compact in the layer near the underlying metal substrate.

Figure 8E:
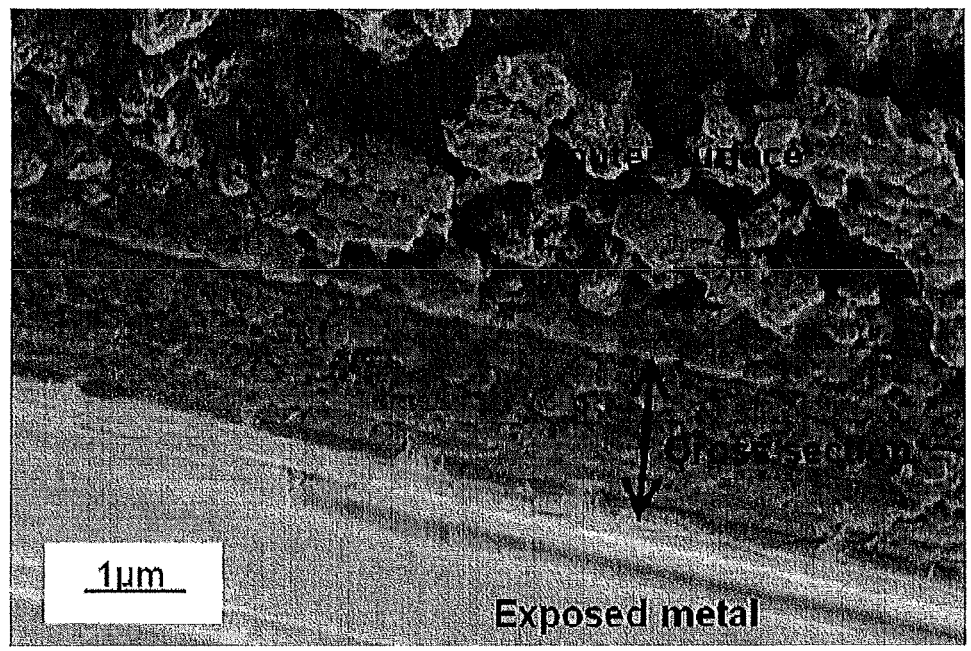
Figure 8F:
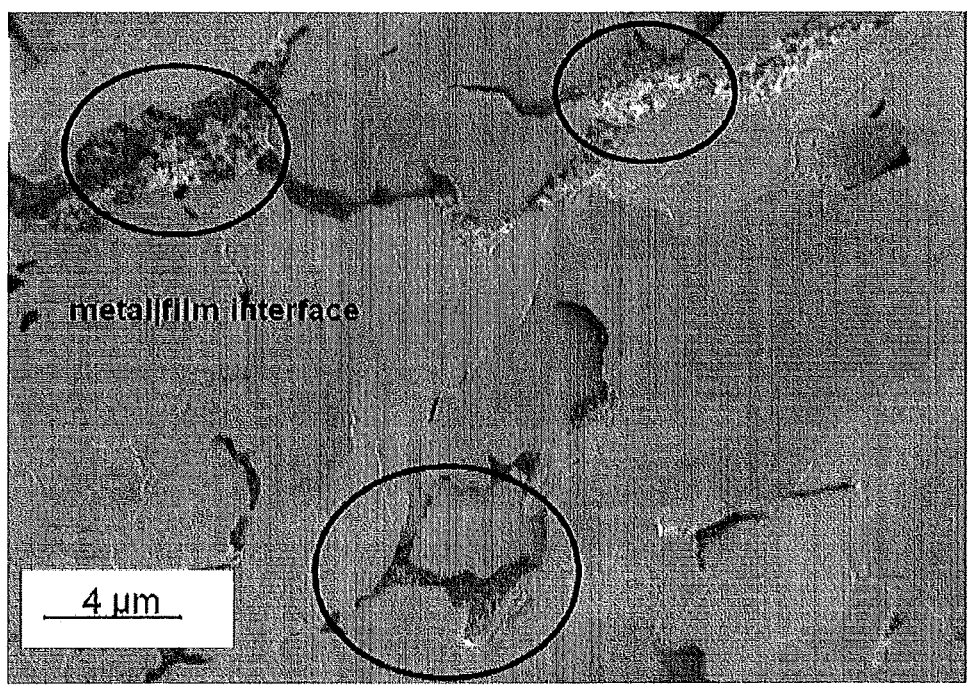

The more dense nature of the sample film at the metal|film interface is evident in FIG. 8*e* and FIG. 8*f*. In FIG. 8*e*, the outer surface is clearly much more porous than the inner layers. In FIG. 8*f*, the sample film was removed with a carbon adhesive used for SEM studies in order to look at the film surface adjacent to the deposition electrode. It can be observed that the metal-film surface is compact and smooth. The gaps where portions of the film remained adherent to the surface of the electrode show that the film is porous towards the outside (shown by circles). The presence of these gaps also attests to the robustness of adhesion of the film, an additional desirable property.

This two layer morphology, which is proposed to be the origin of the observed ohmic behavior, is further supported by the film of PEDOT/$PSS^-$ (FIG. 8*g*). Zooming in on a crack and looking at the film's surface shows that, unlike PEDOT/$BF_4$ films, the film is homogeneously compact. Its outer surface can be described as rough instead of porous. The morphological model, as suggested by these images is congruent with the resulting impedance data. While PEDOT/$BF_4^-$ exhibits ohmic behavior, PEDOT/PSS- lacks that ohmic signature in the frequency range of interest.

Charge Transport in the Two-layer Film:

A proposed equivalent circuit (FIG. 9) for the PEDOT electrode can be described by a hybrid model which combines a resistance capacitance transmission line with an intercalation model (Bisquert, J. *Electrochimica Acta* 2002, 47, 2435-2449), one of which reports the behavior of the compact layer and the other the behavior of the porous layer. Assuming conduction is due to electron (or h+) transport in the compact layer and ionic transport in the porous layer, the behavior of the circuit as a function of frequency shows both a frequency dependent and an ohmic, frequency independent regime with a crossover between the two behaviors at a frequency we refer to as ωo.

When the perturbation frequency is greater than the characteristic frequency, $\omega \gg \omega o$, a frequency-independent impedance originating from ohmic ionic resistance in the pore channels is expected. (Roβberg, K.; Paasch, G.; Dunsch, L.; Ludwig, S. *Journal of Electroanalytical Chemistry* 1998, 443, 49-62) Consideration of the presence of both ionic and electronic (or hole) conduction pathways suggests that charge carriers propagate inwards through the pores of the film if the ionic resistance in the electrolyte is lower than that in the porous layer of the polymer film. This assumption is supported by the increased porosity and disorder, both of which will decrease intrachain conductivity.

Charge transport in the compact layer proceeds primarily through a fast succession of electron exchange reactions which propagate along the chain in the t layer, the situation where the electronic resistance, Re, is smaller than ionic resistance, Ri is assumed. (Ren, X.; Pickup, P. G. *Journal of Electroanalytical Chemistry* 1997, 420, 251-257, Albery, W. J.; Mount, A. R. *Journal of the Chemical Society, Faraday Transactions* 1994, 90, 1115-1119). As such, the electronic charge carriers move toward the polymer|solution interface. An approximation of the polymer|electrolyte interface as a fractal, more specifically a case of the Koch curve model, as treated by Gols and Geertsman (Gols, J. E.; Geertsma, W. *Journal of Physics: Condensed Matter* 1989, 4469) is predicted to result in a constant impedance over a broad frequency due to the double layer capacitance in the pores. Ions that can still move through the channels will contribute an ohmic solution resistance to the circuit. At high frequency ($\omega \gg \omega o$), what would be ordinarily represented by a single charge-carrier type transmission line representing distributed ionic resistance and capacitance can be reduce to a resistance Ri and a constant phase element (CPE) in series, which exhibits an overall resistive behavior. The capacitive behavior resulting from the CPE is only observed at low frequency.

In the low frequency regime, a scenario where $\omega \ll \omega o$, the series CPE1 which represents the capacitive charging/discharging at the x|t layer interface. This interface and associated double layer charging cannot be defined in terms of the well-known Gouy-Chapman-Stern model of the double layer. Counterion diffusion within the more compact film layers can be ignored because ion transport is too slow within those layers to have a noticeable impact on the impedance response. The frequency at which this CPE begins to impact the impedance behavior of the film depends on the ion penetration depth, also determined by the thickness of the x layer.

It may seem unrealistic to assume a double layer charging/discharging within the polymer matrix. However, based on the observed dependence of impedance on morphology, there has to be an ion-blocking layer within the polymer where a charge separation forms. It is reasonable to assume a transition layer exists between the electronic (compact) and ionic (porous) layer which where the conductivity will be through relatively equal ionic and electronic (or h+) mobilities. A rigorous theoretical treatment of impedance characteristics of such a layer by Vorontyntsev et al. predicts a frequency-independent behavior. (Vorotyntsev, M. A.; Daikhin, L. I.; Levi, M. D. *Journal of Electroanalytical Chemistry* 1994, 364, 37-49) Consequently, this layer can be regarded as an extension of the x-layer in the model proposed herein.

The final portion of the proposed circuit includes two parallel RC circuits. One represents the electronic charge transduction resistance, $R_e$, and interfacial capacitance at the polymer|metal film interface. The second represents the conduction in the compact layer.

Theoretically, the t layer should be modeled by an $R_r C_{total}$ circuit where the $R_r$ represent electronic resistance and $C_{total}$ represents capacitive charging caused by trapped counterions. However, this capacitive contribution will be significantly less than those of C1 or CPE1 thus eliminating its effect on the total impedance; $C_{total}$ is negligible.

This very general circuit can produce a variety of Z"/Z' relationships. Theoretically, it should exhibit two semicircles. Depending on the values of the component elements resulting from the film's microstructure (as described above), the semicircles may not be observed in the frequency range probed. In the case of a film with two different morphologies in series, this equivalent circuit approaches the behavior of a resistor in series with a capacitor or CPE (at low frequency). At high and medium frequency, however, an ohmic resistance of 60-100 ohms, approximately that of the ionic solution), should be observed.

In accordance with the proposed circuit, these electrodes exhibit ohmic behavior that spans almost the entire frequency range probed. FIGS. 11-13 show that at low frequency (<10 Hz), the well known capacitive slope, implied in the CPE1 discussed above is observed.

The macro-structural features of the film appear to be responsible for the ohmic behavior in this frequency range. The mechanism includes injection of electronic (or h+) charge carriers from the metal into the polymer with transport of those carriers through the film and into solution that permeates the porous layer. This is supported by the results of variations in deposition time, electropolymerization dopant concentration, and monomer or oligomer concentration described in the next three subsections.

Example 2

Effect of Deposition Time

The effect of electropolymerization times on impedance and its frequency dependence was evaluated using deposition times of 30, 60, 90 and 120 seconds using EDOT monomer or oligomer, where the monomer or oligomer and counterion concentrations were 0.0125 M and 0.1 M, respectively, during polymerization. FIG. 10 compares the Nyquist plot of electrodes produced using different deposition times. Ohmic resistance is almost the same (see IZI values) in the high and intermediate frequency ranges. However, thinner films produced by shorter deposition times not only deviate from near ohmic behavior at higher frequency compared to thicker films, they also exhibit high capacitance at low frequency leading to frequency dependent behavior. Impedance is relatively independent of film thickness in this region over the optimal deposition time range, suggesting that even the thicker films can exhibit the two layer morphology described above. In theory, the longer deposition times should result in a thicker porous (x) layer. However, it appears that the deposition conditions used allow oligomers to be trapped within the inner layer, which subsequently polymerize to fill in the inner-most pores. Proportional growth of the compact layer and porous layer would occur, causing the frequency window for ohmic behavior to remain the same. The contribution of diffusing solution ions and dopants into the compact (t) layer film is slow compared to fast transport of electrons. If ionic diffusion is important, increasing the t-layer thickness would result in Warburg behavior being absent in these films. While a shorter deposition time (30 sec) resulted in a film with a larger capacitive contribution at low frequency (C=40p F/cm² compared to 24 pF/cm² at 0.1 Hz), a longer deposition time (150 sec) resulted in thick, porous and brittle films.

The optimum deposition time is guided by the balance between achieving ohmic behavior within a wider frequency and achieving good mechanical properties of the film. While a shorter deposition time (under 30 seconds) results in a film that exhibits largely capacitive impedance, (C=40 µF/cm² at 0.1 Hz), a deposition time over 120 seconds results in thick, porous and brittle films. The capacitive behavior of the thinner film (electropolymerization time less than and 30 seconds) is consistent with what would be expected when the porous layer is absent in which case the surface would be considered as rough instead of porous.

FIG. 10 compares the Bode plots of electrodes produced using different deposition times. It is obvious that the ohmic resistance is almost the same (see |Z| values) in the high, the medium, and moderately low frequency ranges. However, it is also observed that impedance of thinner films (short electropolymerization time) deviates from ohmic behavior before that of thicker films does. Thin films exhibit higher capacitance at low frequency than thick films as a consequence of their smoother morphology. In this case, the microporosity of the film leads to a high double layer capacitance contribution at medium and low frequency ranges.

Example 3

Effect of Dopant Concentration

With increased solution conductivity during polymerization, a faster rate of nucleation and growth of the film on the electrode surface is likely, leading to a less structured t-layer that contains random polymer aggregates. This causes an increase in the |Z| value as seen in FIG. 11. The counterions have been implicated in inhibition effects on the oxidation of the monomer or oligomer onto the electrode surface when the surface concentration of the oxidized sites on the monomer is low compared to the dopant available from the solution. (González-Tejera, M. J.; Carrillo, I.; Hernández-Fuentes, I. *Synthetic Metals* 1998, 92, 187-195). This will lead to formation of a lower coverage and a less dense initial layer and inhomogeneous growth. An alternative interpretation of the causes of this high impedance hinges on the ionic and electronic (or h+) charge carrier interaction. It is generally agreed that anions can act as binding sites which immobilize the charge carriers with opposite charge (Reghu, M.; Subramanyam, S. V.; Chatterjee, S. *Physical Review B* 1991, 43, 4236). In addition, high electrolyte concentrations make it likely that some counterions may be trapped in the compact layer. These would hinder the hopping of positive charge between neighboring sites and would be expected to contribute to structural deformation, particularly in the t layer, and this would lead to limited interchain transport and observable ionic diffusion transport. Therefore, the suggested explanation of higher impedance under higher counterion concentration is based primarily on the contribution of the counterion's effects on structure disorder of the compact layer and associated hindered electronic transport.

Example 4

Effect of Monomer or Oligomer Concentration

Higher concentrations of the monomer or oligomer should lead to faster initial polymerization rates at the surface of the electrode. This faster deposition rate would be expected to result in a less ordered, less compact, layer adjacent to the surface for a given total charge passed. Disordered regions will act as insulator islands due both to absence of π wavefunction overlap and, even where overlap is maintained, to Peierls distortion. (Heeger, A. *J Phys Chem B* 2001, 105, 8475-8491) This more porous t-layer also would be characterized by smaller noninterconnected pores, increasing the influence of ionic conductivity is more pronounced. This is consistent with the experimental results for 0.05, 0.025 and 0.0125 M monomer deposition solutions shown in FIG. 12. These alterations in structure lead to an increase In impedance modulus with higher monomer concentration. As in the case of electrodes produced at higher counterion concentration, the frequency range within which ohmic behavior is observed is shortened. The higher impedance in the case of a 0.00625 M monomer would appear to be a result of the fact that the monomer concentration has, at this point, reached a value where the rate of production of sufficient oligomer is insufficient to result in the nucleation and growth necessary to produce the required two-layer morphology. It is also important to highlight the fact that at very low frequency, all films appear to exhibit the same low capacitive frequency impedance behavior. These observations suggest that the charging mechanism is the same for these films and is largely determined by the formation of the double layer inside the pores of the film.

Comparison of Model and Experimental Impedance Behavior:

As seen in FIG. 13, the simulated and experimental data show excellent agreement over the range probed.

Example 5

Effect of Identity of Electrically-Conductive Polymer on Electrode Signal Transduction The effects of polymer identity on the ability of the electrode made of platinum wire to provide undistorted signal transduction was evaluated using polycarbazole, PEDOP and PEDOT, where each of the electro-conductive polymers was doped with $BF_4^-$. FIG. 14 shows Bode plots from the platinum modified with PEDOT, PEDOP and polycarbazole. The data were obtained at 0.2 V vs. AgCl in 0.1 M KCl, with a bare Pt wire as the auxiliary electrode. Electrodes made from PEDOT and PEDOP exhibited an extended range of frequency-independent behavior compared to that observed for polycarbazole.

Example 6

Effect of Identity of Electrically-Conductive Substrate on Electrode Signal Transduction The effects of electrically-conductive deposition substrate electrode on the ability of electrodes based on deposition of a PEDOT film was evaluated using carbon, gold and platinum as the electrically-conductive substrates. The electrodes were manufactured using an electropolymerization potential of +1300 mV vs. Ag/AgCl from an acetonitrile solution containing 0.0125 M EDOT and 0.1 M tetrabutylammonium tetrafluoroborate and a 90 s electropolymerization time. The solution conditions for EIS measurements were the same as those described above in the study of the Effect of Electrically-Conductive Polymer on Electrode Signal Transduction. The results presented in FIG. 16 indicate that there is minimal contribution to the impedance due to the substrate/polymer interface for the substrates evaluated.

Example 7

Biocompatibility of the Electrodes

The biocompatibility of electrodes coated with PEDOP or P3MT implanted in the brains of rats was evaluated in rats. Rats were sacrificed 14 days after the electrodes were implanted and slices of the brain were obtained. The slices of brain were analyzed using glial fibrillary antibody protein (GFAP) immunofluorescence response by measuring the area in which fluorescence appeared relative to the total area visualized for a fixed magnification and field of view. The results are shown in FIG. 16, where the error bars indicate the standard error of the mean, based on a one-way ANOVA ($p<0.022$) with 9 sections for each of P3MT and PEDOP and 12 sections for Pt. There was no statistically significant difference between the tissue response for electrodes with a layer of P3MT or PEDOP on Pt. However, there was a statistically significant difference ($p<0.05$) between the tissue response for electrodes with a layer of P3MT or PEDOP on Pt when compared to bare Pt electrodes.

Example 8

Measurement of Seizure Activity

The ability of a PEDOP-modified stainless steel electrode to measure seizure activity in rats was compared to that of a conventional stainless steel electrode or a Pt electrode. The PEDOP-modified stainless steel electrode was prepared using the electropolymerization conditions described above in the example of the Effect of Electrically-Conductive Substrate on Electrode Signal Transduction. Seizure activity was induced using pentylenetetrazole (PTZ). FIG. 17 shows the measurement of seizure activity as detected with a conventional polyimide insulated stainless steel electrode compared to a PEDOP-modified stainless steel electrode. The bandwidth of the PEDOP-modified electrode is improved compared to the conventional polyimide insulated stainless steel electrode, as evidenced by the sharpness and amplitude of the peaks of the PEDOP-modified electrode. Typical biosignal frequency rangs are shown in FIG. 18.

Three specific sets of implantable twisted pair platinum electrodes that had been coated with a film of one of the following three polymers: polyethylenedioxythiophene (PEDOT), poly-3-methylthiphene (P3MT), and Polycarbazole (PCz) were evaluated for sensing of seizure activity. (See, FIG. 19.)

Synthesis of Electrodes used in Implantation:

For biocompatibility studies, substrate electrodes were constructed using the following procedure. A one-inch piece of bare platinum wire (d=250 microns) was soldered to the end of a copper wire and the junction was contained within a capillary. The polymer to be tested was then electropolymerized to the surface of the Pt wire using the deposition parameters for carbazole, PEDOT, and P3MT discussed below. The coated Pt wire was then removed from the end of the glass capillary and rinsed in deionized $H_2O$ before implantation. For monitoring of seizure activity, commercial twisted pair stainless steel or Pt electrodes (Plastic 1) were employed after cleaning with ethanol and DI water. Deposition of each type of polymer was carried out using the optimized conditions determined from the EIS experiments.

Surgical Implantation of PEDOT, Carbazole, and P3MT Electrodes:

A. Pre-surgical Operations and Preparation:

Each Sprague-Dawley rat used in the experiment was first weighed and anesthetized with Equithesin through a lateral Intraperitoneal (IP) injection. The amount of Equithesin used was based approximately on a 2 mL/kg ratio. (Equithesin is a mixture of 10 mL of 50 mg/mL pentobarbital solution, 2.13 g $Mg_2SO_4$, 4.25 g chloral hydrate, 12.45 mL ethanol, 216.6 mL propylene glycol, and 43 mL dd $H_2O$). The rat was then placed in a rat urn (bowl), and monitored every minute until the Equithesin had completely nullified the toe pinch reflex.

At this point, aseptic preparation of the incision site and the surgical field was conducted. The hair surrounding the incision site was shaved off completely and the incision site was swabbed with antiseptic. The surgical field was sterilized and all subsequent instruments placed onto the surgical field were sterilized as well via an autoclave. Lubricant was placed directly onto the eyes of the rat to prevent dryness that may result from longer surgical procedures. The animal was then placed in a Kopf stereotaxic frame.

B. Surgical Implantation of the Electrodes:

An anterior posterior (AP) incision was made from the rat's brow region to the base of its head using a #10 blade attached to a scalpel. Skin and tissue were dissected away to reveal the skull, and bregma coordinates were identified and recorded since all subsequent coordinates were made in reference to this point. Two electrodes were implanted bilaterally in the ventral hippocampus (coordinates to bregma: AP: −3.2 mm, ML: +4.0 mm, DV: −3.0 mm), so that each rat model had one twisted pair platinum electrode and one polymer-coated twisted pair platinum electrode (P3MT or PEDOP) implanted into adjacent hemispheres.

Each electrode was passed through a manually drilled hole in the skull that was then surrounded with an acrylic gel foam. The implanted electrodes were then cemented permanently to the rat's skull with dental acrylic, which was also covered by two stainless steel jeweler's screws which had been inserted into the skull, this providing a further anchor. Care was taken to avoid direct contact between the acrylic with both the rat tissue and skin during the acrylic curing process.

C. EEG Response

After a 48-hour period of monitoring and recovery, the Sprague Dawley rat models were connected to an EEG data recording instrument via the two twisted-pair electrodes that had been implanted bilaterally in the C2 region of the ventral hippocampus. The instrument was calibrated before use and baseline data was obtained and recorded to ensure that the Sprague Dawley rat had reached a sufficient equilibrium. The baseline data measurements for the observations shown in FIGS. 20-23 were obtained with the baseline recorded for a minimum of 10 minutes, while the observations in FIGS. 24-26 were made with a baseline recorded for a minimum of 20 minutes. Intraperitoneal (IP) injection of pentylenetetrazol (PTZ), a muscle convulsant to induce muscle convulsions and minor seizures in each of the rats, was administered following the baseline recordings. PZT was administered so that responses could be measured by the absolute differences between baseline readings and those indicating seizure activity. The dosage was adjusted for the mass of the rat. PTZ is a GABA antagonist whose mechanism of epileptic shock is still unknown. However, previous electrophysiology studies have shown that it acts on the cell membrane to decrease the time between action potentials by increasing the permeability to potassium cations.

Data was obtained and recorded throughout the entire process for both the platinum and polymer-modified P3MT and PEDOP electrodes. After these experiments, the Sprague Dawley rats were euthanized per an approved protocol.

FIG. 20 displays the baseline and ictal recordings from rats with platinum and P3MT electrodes. FIGS. 21-23 display close up views of the baseline and ictal platinum and P3MT recordings for Rat 1 (A), Rat 2 (B) and Rat 3 (C), respectively. In each of the rat models, the P3MT coated-platinum electrode showed an improved signal bandwidth and a faster response than the normal uncoated platinum electrode. These results can be seen in each of the baseline and seizure induced graphs for the individual rats. In each baseline graph, the additional peaks seen may be attributed to normal muscle movements in the rat or artifacts from the EEG data recording equipment.

The results for each EEG reading were also in accordance with the expected physiological results. After injection of pentylenetetrazol (PTZ), each rat model showed excursions in potential which can be attributed to the neural firing due to the induction of muscle convulsions.

Figure 26:
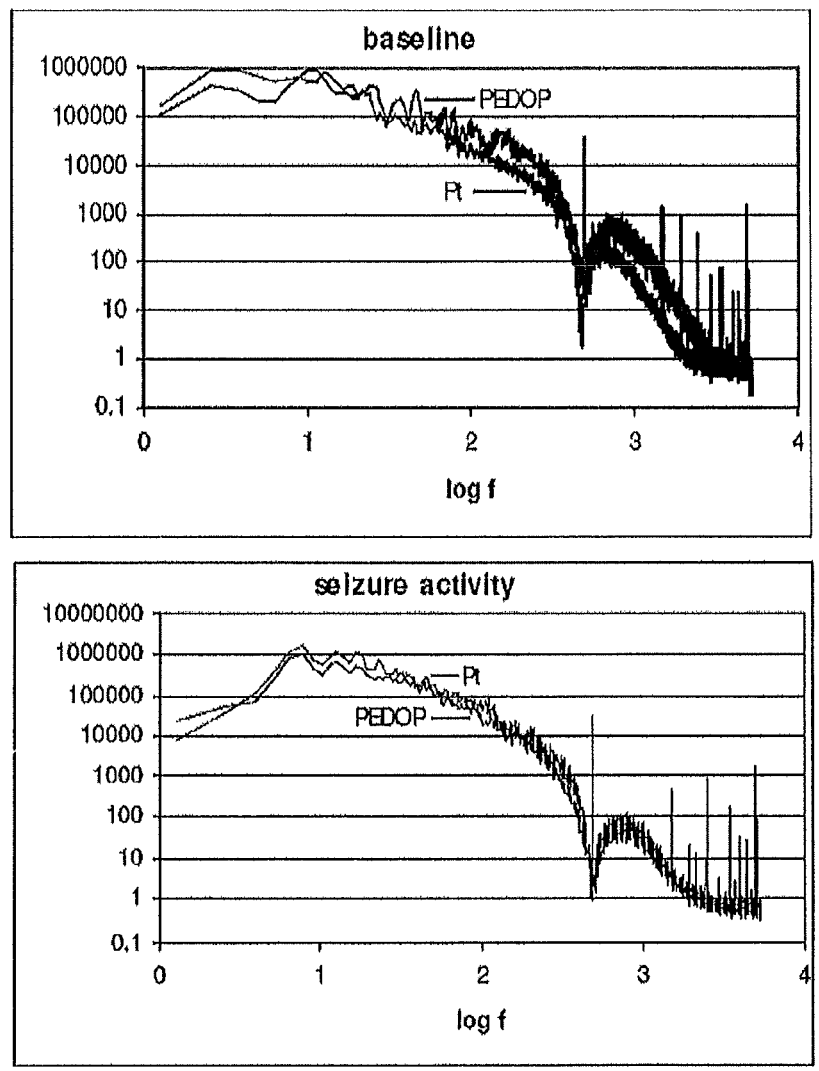
FIG. 26 shows a comparison of signal throughput during EEG data acquisition in log-log format for PEDOP vs Pt electrodes.

FIGS. 24 and 25 show a comparison of signal throughput at f<100 Hz for P3MT vs Pt electrodes and for PEDOP vs Pt electrodes, respectively. FIG. 26 shows a comparison of signal throughput during EEG data acquisition in log-log format for PEDOP vs Pt electrodes.

These studies demonstrate that the use of the electrodes described herein have advantages over currently used electrodes in terms of both electrical response and biocompatibility.

Examples 9-14 relate to embodiment where the electrically-conductive polymer in the electrodes comprises a fiber. FIG. 3 shows a schematic of an embodiment of flow-cell setup for producing electrodes having a fiber that was sued in the following examples.

Example 9

Effect of the Flow Rate of the Monomer or Oligomer Solution on the Production of Microfibers Attached to the Electrically-Conductive Polymer on the Electrodes The volume flow rate and the diameter of the reaction region both impact the linear flow rate past the tip of the deposition electrode. At high flow rates, multiple-ribbon-like fibers were produced not only at the tip but also along the length of the electrode (FIG. 27). However, at lower flow rates there were fewer fibers, and these tended to extend out from the deposition electrode in the direction of flow. For a given volume flow, the fiber diameter decreased significantly as the reaction region diameter decreased. In order to determine the nature of the flow of the solution past the end of the electrode, the Reynolds number was calculated. It was found to be approximately 2100, which falls in the region between laminar flow and turbulent flow.

Example 10

Effect of Electrode Diameter and Interelectrode Separation on the Production of Microfibers Attached to the Electrically-Conductive Polymer Film on the Electrodes The diameter of the deposition electrode and its distance from the counter electrode affected the relative probability that a single fiber would be produced from the end of the working electrode vs. a large number of fibers forming at the tip or along the sides. Decreasing the tip diameter resulted in a significant decrease in the diameter of the fiber produced under the same flow and concentration conditions. Cutting the end of the electrodes at an angle to produce a non-circular cross section at the tip further increased the likelihood of producing a single fiber off the end. The separation between the electrodes had a major impact on the aspect ratio of the fibers produced. At the upper end of the range tested, longitudinal growth was slow and the diameter of the fibers increased.

Example 11

Effect of Dopant Concentration on the Production of Microfibers Attached to the Electrically-Conductive Polymer Film on the Electrodes Electrolyte concentrations that produced the highest-quality fibers (small uniform diameter, single fiber with high aspect ratio) occurred in the midrange of the values used (0.05-0.2 M). At low dopant concentrations (all other parameters remaining constant), the potential drop (and resulting decrease in effective applied potential at the working electrode) resulted in a slower deposition, and at the lowest concentrations, growth was not observed even after several hours.

Example 12

Effect of the Applied Potential and Deposition Time on the Production of Microfibers Attached to the Electrically-Conductive Polymer in the Electrodes The applied potential profoundly affects the kinetics of the deposition process. Potentials at the more positive end of the range tested resulted in rapid fiber growth from the tip. However, if the reaction is allowed to proceed at the same accelerated rate after the initial rapid formation of the fiber, polymer is deposited preferentially on the sides of the fiber (as opposed to the tip) and the diameter begins to increase. In addition, fibers begin to grow from nucleation sites along the length of the electrode.

Example 13

Effect of the Deposition Substrate on the Production of Microfibers Attached to the Electrically-Conductive Polymer in the Electrodes The identity of the substrate electrode influences the ruggedness of the interface between the deposition electrode and the fiber and the time required for initiation of polymer formation. For example, fiber production from gold wires resulted in easily dislodged fibers. Growth from stainless steel electrodes produced a marginally more rugged interface and that from Pt was the most robust.

Example 14

Spectroscopic and Electrochemical Characterization of the Microfibers Attached to the Electrically-Conductive Polymer on the Electrodes Polypyrrole and poly-N-methylpyrrole fibers produced using the optimized parameters above were characterized by Fourier transform IR (FTIR) spectroscopy to confirm the identity of the fibers produced. FIG. 28 shows the FTIR of a poly-N-methylpyrrole fiber. The spectra exhibited the expected C≡C single and double bond stretches at 1540 and 1488 cm$^{-1}$, respectively, and for pyrrole the 1036 cm$^{-1}$ N—H bending mode is present. The electrodes were characterized using CV in 0.050 M ferri-/ferrocyanide in 0.1 M KCl to assess their electrochemical utility. The behavior of the ferri-/ferrocyanide system on poly(N-methylpyrrole) fibers is shown in FIG. 29, which shows a CV of 50 mM ferricyanide in 0.1 M KCl at the poly-N-methylpyrrole electrode. The peak separation ($\Delta E$) is slightly greater than that seen under ideal conditions, but the low background suggests that the electrodes are electrochemically useful. The current density vs. voltage dependence is also not sigmoidal as would be expected for electrodes with this surface area. Both of these deviations from the expected behavior can be explained by slight retardation of electron-transfer kinetics.

FIG. 30 shows a long, thin, poly-N-methylpyrrole fiber produced using conditions in Table II. FIG. 31 shows another long fiber of poly-N-methylpyrrole that extended out from the tip of the working electrode. The latter fiber was produced using the conditions in Table II, but with a deposition time of about 1 hour. The fiber had an overall length of about 4.2 mm. The fiber consisted of a major fiber with a smaller ribbonlike structure wrapping around it for about 550 µm down the fiber from the electrode. This ribbon extended away from the fiber and then terminates. Beyond this point, the main fiber had a uniform rod structure with a 5 µm diameter. It had no discernable surface features even when examined under high magnification as shown in FIG. 32. Electrodes were also produced by polymerization of 3-methylthiophene or aniline using this method. Other dopants used have included dodecylbenzene sulfonate, chloride, perchlorate, tetrafluoroborate, and polymethylmethacrylate.

Microspectroscopic studies were carried out on a fiber produced from 3-methylthiophene/dodecyl-benzenesulfonate solution, which contrasted the film on the surface of the platinum substrate with the fiber on its tip. The fiber showed a significant enhancement of fluorescence when excitation was carried out at 514.5 nm compared to film that is deposited along the sides of the anode.

The effects of the identity of the dopant counterion lie primarily in the flexibility and the chemical stability of the polymer fiber produced, while the effect of the substrate electrode appeared in the durability of the substrate/fiber junction and in the rate of production of the fiber. For example, fibers produced at the platinum substrate grew to a few micrometers in length within 5 min and resulted in a robust interface at the electrode-fiber junction.

Electrodes were prepared by electrodeposition of poly-3-methylthiophene (P3MT) or polyethylenedioxythiophene (PEDOT) onto wires using the procedure described above. FIG. 33 shows a SEM of P3MT on Pt. A uniform P3MT coating appeared within 5 min, with surface features about 1.5 µm diameter and with fibers growing along the length of the electrodes. These fibers, when examined under higher magnification, were smooth with no discernable features, much like those produced in the film-growth experiments. When the coating was allowed to grow for an extended period of time to a thickness of approximately 100 µm, the surface features grew into a spongelike material (FIG. 33).

Raman spectroscopy, obtained with excitation at 785 nm (FIG. 34), was employed to verify the identity and probe the doping levels in the films made with P3MT. The relative location of these peaks corresponds to those previously reported in the literature. (F. Chen, G. Shi, J. Zhang and M. Fu, *Thin Solid Films,* 424, 283, 2003). The slight differences in intensities and positions can be attributed to a difference in the fractional doping in the sample. The doping level of the film, y, can be estimated using the following equation:

$$0.087y - 2.279 = \ln(I_{ox}/I_{red})$$

Based on the intensities at 1422 and 1480 wavenumbers (the peaks for the reduced and oxidized forms respectively), the doping level was estimated to be approximately 23%.

Thin films of PEDOT were manufactured and evaluated as described above. FIG. 35 shows a SEM of PEDOT on Pt. The PEDOT films had surface features similar in shape to those of P3MT films, but they were larger in size The resulting features are about 5-10 µm in diameter. FIG. 36 shows a PEDOT Raman spectra of the PEDOT film. The major spectroscopic features of this film correspond to those previously reported. (William W. Chiu, J. T. S. Cacute, and R. P. C. G. A. Bowmaker, *J. Raman Spectrosc.,* 37, 1354 (2006).

Using the procedures described above, robust fibers with diameters of about 5-6 µm or less were produced from 3-methylthiophene and N-methylpyrrole. The surface of the fibers is smooth on the scale of tens of nanometers, and there are no visible voids on this scale. Polypyrrole fiber growth can be controlled by varying the process parameters which govern the transport and flow pattern of the electrolyte across the electrode as described above. P3MT fibers with the same range of diameters can be produced by the same general procedure. The fibers are not subject to the formation of cracks or voids, even after several months in a storage container, as evidence by SEM analysis.

While exemplary articles and methods have been described in detail with reference to specific embodiments thereof, it will be apparent to those skilled in the art that various changes and modifications can be made, and equivalents employed without departing from the scope of the pending claims.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A polymer film electrode comprising:
   (i) an electrically-conductive substrate; and
   (ii) an electrically-conductive polymer applied to said electrically-conductive substrate, wherein said electrically-conductive polymer is in electrical contact with said electrically-conductive substrate, and said electrode exhibits ohmic behavior over a range of about 800 Hz to about 100 kHz; wherein the electrode further exhibits ohmic behavior over at least one range selected from the group consisting of: 50 Hz to 100 Hz, 25 Hz to 50 Hz, 10 Hz to 50 Hz, 5 Hz to 50 Hz, 10 Hz to 25 Hz, 5 Hz to 25 Hz, 1 Hz to 25 Hz, 5 Hz to 10 Hz, and 1 Hz to 10 Hz;
   wherein said electrically-conductive polymer is a compact layer that is not permeable to a solution adjacent to the electrode and is overlaid with a structure that is ionically permeable.

2. The polymer film electrode of claim 1, wherein said electrically-conductive polymer comprises at least one member selected from the group consisting of a polythiophene, a polypyrrole, a polyaniline, a polycarbazole, a poly(diallyldimethylammonium chloride), a poly-4-vinylpyridine, a poly(vinylalcohol), a polymer blend thereof, and combinations thereof and wherein said electrically-conductive polymer optionally comprises one or more dopants.

3. The polymer film electrode of claim 1, wherein said electrically-conductive substrate comprises a first electrically-conductive substrate portion and a second electrically-conductive substrate portion different therefrom,
wherein said first electrically-conductive substrate portion is at least partially coated by said second electrically-conductive substrate portion, and
wherein said second electrically-conductive substrate portion comprises at least one metal selected from the group consisting of platinum, gold, silver, iridium, palladium, tungsten, nickel, copper, aluminum, stainless steel, zinc, titanium, tungsten, an oxide thereof, an alloy thereof and combinations thereof.

4. The polymer film electrode of claim 3, wherein said first electrically-conductive substrate portion comprises platinum, said second electrically-conductive substrate portion comprises gold and said electrically-conductive polymer comprises at least one member selected from the group consisting of polyalkoxythiophenes, polyalkylthiophenes, polyalkoxypyrroles, N-substituted polypyrroles, polycarbazole and N-substituted polycarbazoles, and combinations thereof.

5. The polymer film electrode of claim 1, wherein the thickness of said compact layer and said structure that is ionically permeable together is less than about 10 microns.

6. The polymer film electrode of claim 1, wherein said polymer film electrode is of a size in a range from about 0.1 to about 1 micron or in a range from about 1 to about 10 microns, and wherein said polymer film electrode is sized to fit within a biological cell.

7. The polymer film electrode of claim 2, wherein (a) said electrically-conductive substrate comprises a metal, a non-metallic electrically-conductive substance, or combinations thereof.

8. The polymer film electrode of claim 2, wherein said electrically-conductive substrate is in the form of a wire core, a planar disk or a ring.

9. The polymer film electrode of claim 2, wherein said electrically-conductive substrate comprises at least one material having a work function greater than the work function of the electrically-conductive polymer.

10. The polymer film electrode of claim 2, wherein said electrically-conductive substrate comprises at least one metal selected from the group consisting of platinum, gold, silver, iridium, palladium, tungsten, nickel, copper, aluminum, stainless steel, zinc, titanium, tungsten, an oxide thereof, an alloy thereof, and combinations thereof.

11. The polymer film electrode of claim 2, wherein said electrically-conductive substrate comprises at least one member selected from the group consisting of a carbon nano-wire, a carbon fiber, a glassy carbon rod, a carbon composite, a conductive ceramic, a conductive monomer or oligomer, a conductive polymer, and combinations thereof.

12. The polymer film electrode of claim 4, wherein said electrically-conductive polymer comprises PEDOT and a dopant that comprises tetrafluoroborate or perchlorate.

* * * * *